US005914109A

United States Patent [19]
Zolla-Pazner et al.

[11] Patent Number: 5,914,109
[45] Date of Patent: Jun. 22, 1999

[54] HETEROHYBRIDOMAS PRODUCING HUMAN MONOCLONAL ANTIBODIES TO HIV-1

[75] Inventors: Susan Zolla-Pazner, New York; Miroslaw K. Gorny, Forest Hills, both of N.Y.

[73] Assignee: New York University, New York, N.Y.

[21] Appl. No.: 08/345,321

[22] Filed: Nov. 21, 1994

Related U.S. Application Data

[63] Continuation of application No. 07/872,675, Apr. 23, 1992, abandoned, which is a continuation-in-part of application No. 07/538,451, Jun. 15, 1990, abandoned, and application No. 07/684,090, Apr. 12, 1991, abandoned, which is a continuation-in-part of application No. 07/538,451, Jun. 15, 1990, abandoned.

[51] Int. Cl.$^6$ .......................... A61K 39/395; C07K 16/10
[52] U.S. Cl. ...................................... 424/133.1; 424/142.1; 424/148.1; 424/160.1; 435/69.6; 435/70.21; 435/172.2; 435/328; 435/339.1; 530/387.3; 530/388.15; 530/388.35
[58] Field of Search ............................. 424/136.1, 142.1, 424/148.1, 160.1, 133.1; 435/69.6, 69.7, 70.21, 172.2, 172.3, 328, 320.1, 252.3, 252.33, 339.1; 530/387.3, 388.15, 388.35; 536/25.53

[56] References Cited

U.S. PATENT DOCUMENTS 4,725,669  2/1988  Essex et al. .

FOREIGN PATENT DOCUMENTS

| 0255190 | 1/1987 | European Pat. Off. . |
| 0311228 | 3/1988 | European Pat. Off. . |
| 0311219 | 7/1988 | European Pat. Off. . |
| 0306219 | 8/1988 | European Pat. Off. . |
| 0328403 | 2/1989 | European Pat. Off. . |
| 8702775 | 5/1987 | WIPO . |
| 8809181 | 1/1988 | WIPO . |
| 8805825 | 2/1988 | WIPO . |

OTHER PUBLICATIONS

Fahey et al., "Status of Immune Based Therapies in HIV Infection and AIDS," Clin. Exp. Immunol. 88:1–5, Apr. 1992.
Fox, J.L., "No Winners Against AIDS," Biol Technology 12:128, Feb. 1994.
Casali et al., Science 234:476–9, 1986.
Rudikoff et al PNAS USA 79:1979–83 1982.
Morrison Science 229:1202–1207, 1985.
Gorny et al. PNAS USA 86:1624–1628 Mar. 1989.
Javaherian et al. Science 250:1590–1593, 1990.
Teng et al. PNAS USA 80:7308–7312, 1983.
Goudsmit et al., AIDS 2(3):157–164 1988.
Robinson et al, AIDS Res Hum Retroviruses 6(5):567–79 May 1990.
Karwowska et al. in Vaccines 92, Brown et al. Eds. CSHL Press 1992.

Zolla–Pazner, et al., "Production of Human Monoclonal Antibodies Against the V3 Loop of gp120", Sixth Int. Conference on AIDS, UCSF, San Francisco, Jun. 21, 1990— Abstract Th.A.75.
Grunow, R. et al., "The High Efficiency, Human B Cell Immortalizing Heteromyeloma CB–F7", Journal of Immunological Methods, 106(2):257–265 (Feb. 10, 1988).
Akerblom, et al., "Neutralizing Cross–Reactive and Non–Neutralizing Monoclonal Antibodies to HIV–1 gp120", AIDS 4:953–960 (1990).
Berman, P. et al., "Protection of Chimpanzees from Infection of HIV–1 After Vaccination with Recombinant Glycoprotein gp120 but not gp160", Nature 345:622–625 (1990).
Emini, E. et al., "Antibody–Mediated in Vitro Neutralization of Human Immunodeficiency Virus Type 1 Abolishes Infectivity for Champanzees" J. Virol 64(8):3674–3678 (1990).
Girard, M. et al., "Immunization of Chimpanzees Confers Protection Against Challenge with Human Immunodeficiency Virus" Proc. Natl. Acad. Sci. USA 88:542–546 (1991).
Jackson, et al., "Passive Immunoneutralisation of Human Immunodeficiency Virus in Patients with Advanced AIDS", The Lancet ii:647 (1988).
Karpas, et al. "Effects of Passive Immunization in Patients with the Acquired Immunodeficiency Syndrome–Related Complex and Acquired Immunodeficiency Syndrome" Proc. Natl. Acad. Sci. USA 85:9234–9237 (1988).
Ohlin, et al., "Human Monoclonal Antibodies Against a Recombinant HIV Envelope Antigen Produced by Primary In Vitro Immunization" Immunology 68:325–331 (1989).
Ohno, et al., "A Broadly Neutralizing Monoclonal Antibody that Recognizes the $V_3$ Region of Human Immunodeficiency Virus Type 1 Glycoprotein gp120" Proc. Natl. Acad. Sci. USA 88:10726–10720 (1991).
Prince, et al., "Prevention of HIV Infection by Pasisve Immunization with HIV Immunoglobulin" Aids Research and Human Retroviruses 7(12):971–973 (1991).

(List continued on next page.)

Primary Examiner—Robert D. Budens
Attorney, Agent, or Firm—Browdy and Neimark

[57] ABSTRACT

Heterohybridomas producing human monoclonal antibodies against a neutralizing epitope of HIV-1 are prepared by transforming peripheral blood lymphocytes by Epstein-Barr virus, selecting cells producing an antibody to a synthetic peptide representing part of the neutralizing epitope, and fusing them with a heteromyeloma cell. A method for producing a human monoclonal antibody specific for a neutralizing HIV-1 epitope from the heterohybridoma is disclosed. Also provided are human neutralizing monoclonal antibodies specific for particular peptide epitopes of the V3 loop of the gp120 glycoprotein of HIV, in particular a broadly reactive antibody specific for diverse HIV-1 strains, preferably recognizing an epitope comprising an amino acid sequence GPXR or GRAF.

14 Claims, 15 Drawing Sheets

OTHER PUBLICATIONS

Rusche, et al., "Antibodies that Inhibit Fusion of Human Immunodeficiency Virus–Infected Cells Bind a 24–Amino Acid Sequence of the Viral Envelope, gp120" *Proc. Natl. Acad. Sci. USA* 85:3198–3202 (1988).

Scott, et al., "Human Monoclonal Antibody that Recognizes the V3 Region of Human Immunodeficiency Virus gp120 and Neutralizes the Human T–Lymphotropic Virus Type III$_{MN}$ Strain" *Proc. Natl. Acad. Sci. USA* 87:8597–8601 (1990).

Berzofsky, J. et al. "Development of Artificial Vaccines Against HIV Using Defined Epitopes" *The FASEB Journal* 5:2414–2418 (1991).

Berzow, D. et al, "Human Monoclonal Antibodies to HIV" *Proc. Vth Int'l AIDS Conf.,* Montreal, 1989, abstr. TCP 150.

Chanh, T. et al., "Induction of Anti–HIV Neutralizing Antibodies by Synthetic Peptides" *EMBO J.* 5:3065–3071 (1986).

Goudsmit, J. et al., "Human Immunodeficiency Virus Type 1 Neutralization Epitope with Conserved Architecture Elicits Early Type–Specific Antibodies in Experimentally Infected Chimpanzees" *Proc. Natl. Acad. Sci. USA* 85:4478–4482 (1988).

Ho, D. et al., "Conformational Epitope on gp120 Important in CD4 Binding and Human Immunodeficiency Virus Type 1 Neutralization Identified by a Human Monoclonal Antibody" *J. Virol.* 65(1):489–493 (1991).

Kang, C et al., "Evidence for non–V3–Specific Neutralizing Antibodies that Interfere with gp120/CD4 Binding in Human Immunodeficiency Virus 1–Infected Humans" *Proc. Natl. Acad. Sci. USA* 88:6171–6175 (1991).

LaRosa, G. et al., "Conserved Sequence and Structural Elements in the HIV–1 Principal Neutralizing Determinant" *Science* 249:932–935 (1990).

Nara, P. et al., "Emergence of Viruses Resistant to Neutralization by V3–Specific Antibodies in Experimental Human Immunodeficiency Virus Type 1 IIIB Infection of Chimpanzees" *J. Virol.* 64(8):3779–3791 (1991).

Putkonen, P. et al., "Prevention of HIV–2 and SIV$_{sm}$ Infection by Passive Immunization in Cynomolgus Monkeys" *Nature* 352:436–438 (1991).

Karwowska, S. et al., "Relation Between Cross–Reactivity and Affinity of Human Monoclonal Antibodies (HumAbs) to Synthetic Peptides of the V3 Loop of Divergent HIV Strains", *VII International Conference on AIDS,* Florence Jun. 16–21, 1991, vol. 2, Abstract #W.A.1318, p. 171.

Gorny, M.K., et al., "Human Monoclonal Antibodies (HumAbs) to the V3 Loop of HIV–1 React with Divergent Strains", *VII International Conference on AIDS,* Florence Jun. 16–21, 1991, vol. 2, Abstract #W.A.1319 p. 171.

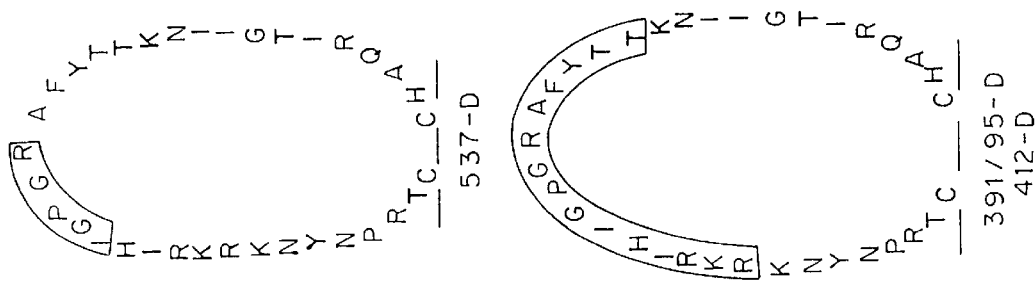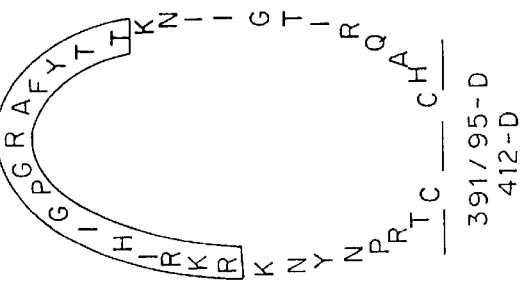
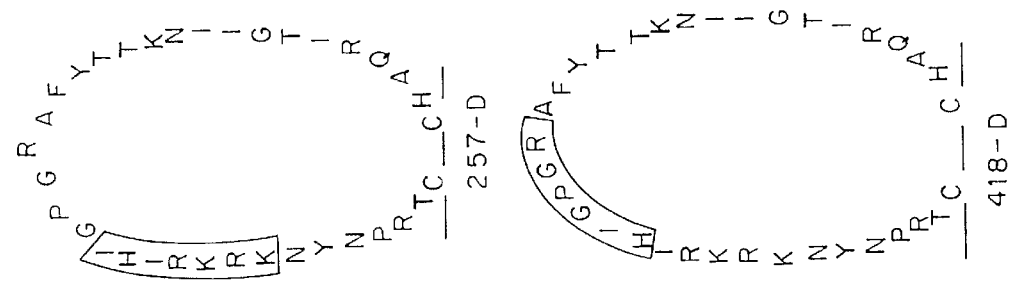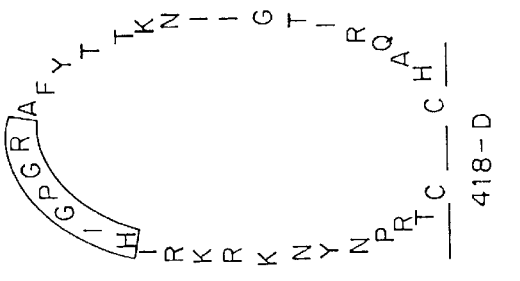
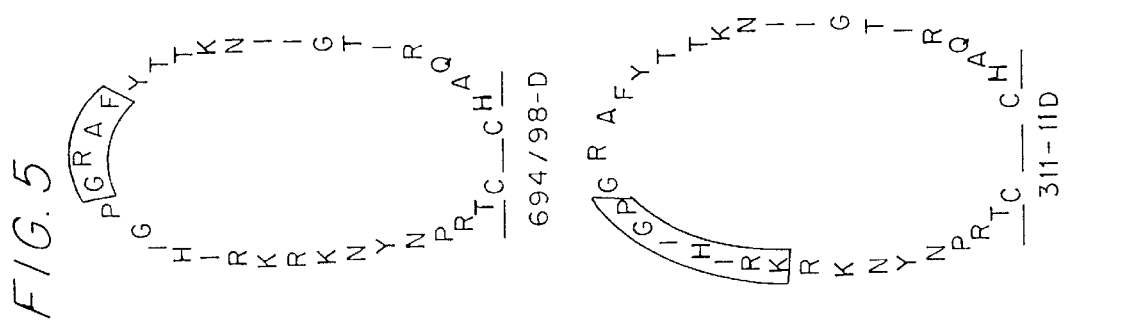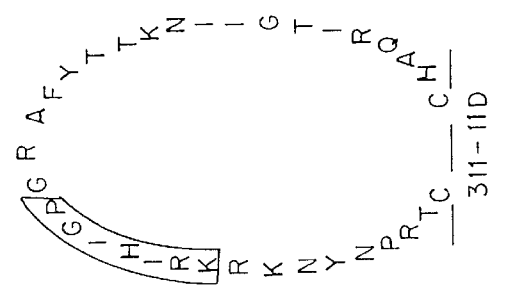
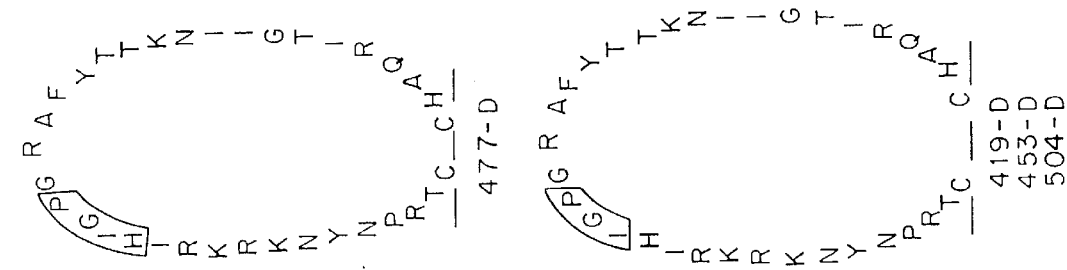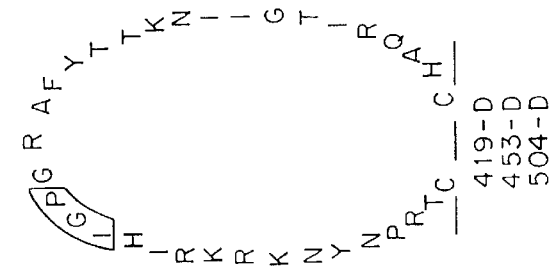
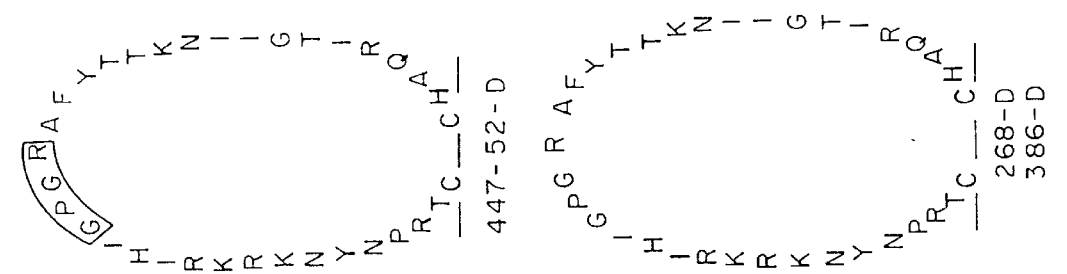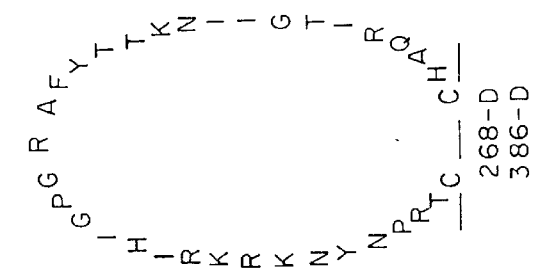
FIG. 5

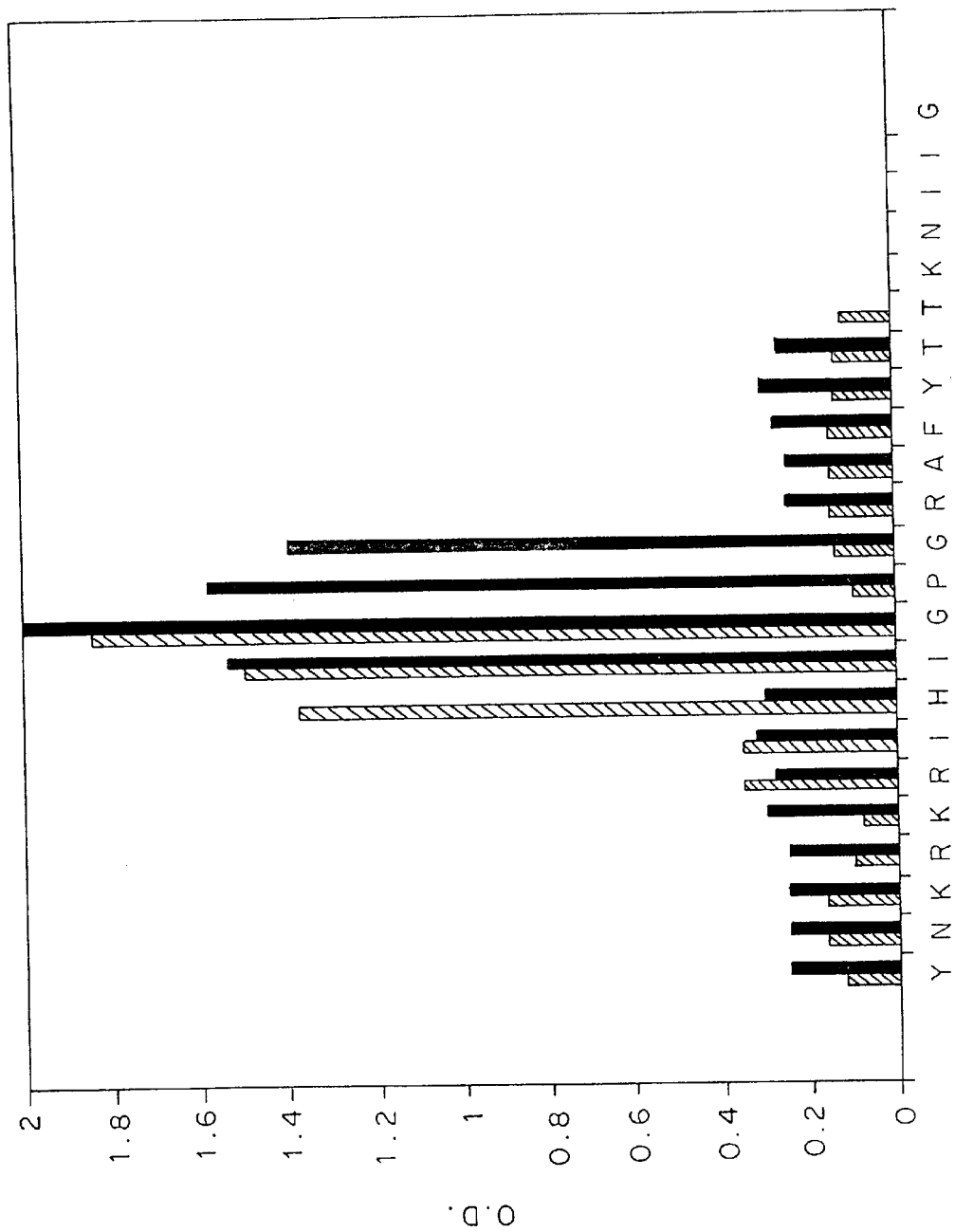

```
      ATGGCCGGCTCCCCTCTCCTCCTCACCCTTCTCATTCACTGCACAGGGTCCTGGGCCCAG
   3  ------+---------+---------+---------+---------+---------+---   62
      TACCGGCCGAGGGGAGAGGAGGAGTGGGAAGAGTAAGTGACGTGTCCCAGGACCCGGGTC
                                                                     +1
c:    MetAlaGlySerProLeuLeuThrLeuLeuIleHisCysTHrGlySerTrpAlaGln       -

TCTGTGTTGACGCAGCCGCCCTCAGTGTCTGCGGCCCCAGGACAGAAGGTCACCATCTCC
  63  ------+---------+---------+---------+---------+---------+---  122
      AGACACAACTGCGTCGGCGGGAGTCACAGACGCCGGGGTCCTGTCTTCCAGTGGTAGAGG c:    SerValLeuThrGlnProProSerVlaSerAlaAlaProGlyGlnLysValThrIleSer    -

TGCTCTGGAAGCAGCTCCAACATTCCCAATAATTATGTATTGTGGTACCACCAGTTCCCA
 123  ------+---------+---------+---------+---------+---------+---  182
      ACGAGACCTTCGTCGAGGTTGTAAGGGTTATTAATACATAACACCATGGTCGTCAAGGGT c:    CysSerGlySerSerSerAsnIleGlyAsnAsnTyrValLeuTrpTyrGlnGlnPhePro    -

GGAACAGCCCCCAAACTCCTCATTTATGGCAATAATAAGCGACCCTCAGGGATTCCTGAC
 183  ------+---------+---------+---------+---------+---------+---  242
      CCTTGTCGGGGGTTTGAGGAGTAAATACCGTTATTATTCGCTGGGAGTCCCTAAGGACTG c:    GlyThrAlaProLysLeuLeuIleTyrGlyAsnAsnLysArgProSerGlyIleProAsp    -

CGATTCTCTGGCTCCAAGTCTGGCACGTCAGCCACCCTGGGCATCACCGGACTCCAGACT
 243  ------+---------+---------+---------+---------+---------+---  302
      GCTAAGAGACCGAGGTTCAGACCGTGCAGTCGGTGGGACCCGTAGTGGCCTGAGGTCTGA c:    ArgPheSerGlySerLysSerGlyThrSerAlaThrLeuGlyIleThrGlyLeuGlnThr    -

GGGGACGAGGCCGATTATTTCTGCGCAACATGGGATACCCCCCTGAGTGCTGATTGGGTG
 303  ------+---------+---------+---------+---------+---------+---  362
      CCCCTGCTCCGGCTAATAAAGACGCGTTGTACCCTATCGCCGGACTCACGACTAACCCAC c:    GlyAspGluAlaAspTyrPheCysAlaThrTrpAspSerGlyLeuSerAlaAspTrpVal    -

TTCGGCGGAGGGACCAAGCTGACCGTCCTAAGTCAT
 363  ------+---------+---------+-------   398
      AAGCCGCCTCCCTGGTTCGACTGGCAGGATTCAGTA c:    PheGlyGlyGlyThrLysLeuThrValLeuSerHis                            -
```

Enzymes that do cut:

NONE

Enzymes that do not cut:

EcoRI
FCRFV1$

```
     ATGGTGTTTGGGCTGAGCTGGATTTTCCTCGCTGCTATTTTAAAAGGTGTCCAGTGTGAG
   4 ------+---------+---------+---------+---------+---------+---  63
     TACCACAAACCCGACTCGACCTAAAAGGAGCGACGATAAAATTTTCCACAGGTCACAcTC
                                                                +1
a:   MetValPheGlyLeuSerTrpIlePheLeuAlaAlaIleLeuLysGlyValGlnCysGlu    -

GTGCAGCTGGTGGAGTCTGGGGGAGGCTTGGTAAAGCCTGGGGGGTCCCTCAGACTCACC
  64 ------+---------+---------+---------+---------+---------+--- 123
     CACGTCGACcaccTCAGACCCCCTCCGAACCATTTCgGACCCCCCAGGGAGTCTGAGTGG a:   ValGlnLeuValGluSerGlyGlyGlyLeuValLysProGlyGlySerLeuArgLeuThr    -

TGTGTAGCCTCTGGTTTCACGTTCAGTGATGTCTGGCTGAACTGGGTCCTCCAGGCTCCA
 124 ------+---------+---------+---------+---------+---------+--- 183
     ACACATCGGAGACCAAAGTGCAAGTCACTACAGACCGACTTGACCCAGGAGGTCCGAGGT a:   CysValAlaSerGlyPheThrPheSerAspValTrpLeuAsnTrpValLeuGlnAlaPro   -

GGGAAGGGGCTGGAGCGGGTCGGCCGTATTAAAAGCAGAACTGATGGTGGGACAACAGAC
 184 ------+---------+---------+---------+---------+---------+--- 243
     CCCTTCCCCGACCTCGCCCAGCCGGCATAATTTTCGTCTTGACTACCACCCTGTTGTCTG a:   GlyLysGlyLeuGluArgValGlyArgIleLysSerArgThrAspGlyGlyThrThrAsp   -

TACGCTGCATCCGTGaaaggcagattcaccatctcaagagatgactcaaaaaacacgcta
 244 ------+---------+---------+---------+---------+---------+--- 303
     ATGCGACGTAGGCACtttccgtctaagtggtagagttctctactgagttttttgtgcgat a:   TyrAlaAlaSerValLysGlyArgPheThrIleSerArgAspAspSerLysAsnThrLeu   - tatctgcaaatgaatagcctgaaaaccgaggacacagccgtttattcctgcaccacagat
 304 ------+---------+---------+---------+---------+---------+--- 363
     atagacgtttacttatcggacttttggctcctgtgtcggcaaataaggacgtggtgtcta a:   TyrLeuGlnMetAsnSerLeuLysThrGluAspThrAlaValTyrSerCysThrThrAsp   - ggttttattatgattcggggagtctccgaggactactactactactacATGGACGTTTGG
 364 ------+---------+---------+---------+---------+---------+--- 423
     ccaaaataatactaagcccctcagaggctcctgatgatgatgatgatgTACCTGCAAACC a:   GlyPheIleMetIleArgGlyValSerGluAspTyrTyrTyrTyrTyrMetAspValTrp   -

CCCAAACCCACCACGGTCACCGTgagCTCA
 424 ------+---------+---------+--- 453
     CCGTTTCCCTGGTGCCAGTGGCActcGAGT a:   GlyLysGlyThrThrValThrValSerSer    -
```

```
    ATGGCCGGCTCCCCTCTCCTCCTCACCCTCCTCACTCTCTGCACAGGCTCTGAGGCCTCC
 1  ------------+---------+---------+---------+---------+---------+  60
    TACCGGCCGAGGGGAGAGGAGGAGTGGGAGGAGTGAGAGACGTGTCCGAGACTCCGGAGG
```
a:  MetAlaGlySerProLeuLeuLeuThrLeuLeuThrLeuCysThrGlySerGluAlaSer   -

```
    TATGAGCTGACACAGCCACCCTCGGTGTCAGTGTCCCCTGGACAGACGGCCAGGATCACC
 61 ------------+---------+---------+---------+---------+---------+  120
    ATACTCGACTGTGTCGGTGGGAGCCACAGTCACAGGGGACCTGTCTGCCGGTCCTAGTGG
```
a:  TyrGluLeuThrGlnProProSerValSerValSerProGlyGlnThrAlaArgIleThr   -

```
    TGTTCTGGAGATGCATTGCCAAACCAATATGTTTATTGGTACCAACAGAGACCAGGCCAG
121 ------------+---------+---------+---------+---------+---------+  180
    ACAAGACCTCTACGTAACGGTTTGGTTATACAAATAACCATGGTTGTCTCTGGTCCGGTC
```
a:  CysSerGlyAspAlaLeuProAsnGlnTyrValTyrTrpTyrGlnGlnArgProGlyGln   -

```
    GCCCCTGTGGTGGTCCTATATAAAGACACTGAGAGGCCCTCAGGGATCCCTGAGCGATTC
181 ------------+---------+---------+---------+---------+---------+  240
    CGGGGACACCACCAGGATATATTTCTGTGACTCTCCGGGAGTCCCTAGGGACTCGCTAAG
```
a:  AlaProValValValLeuTyrLysAspThrGluArgProSerGlyIleProGluArgPhe   -

```
    TCTGGCTCCAGCTCAGGGACAACAGTCACGTTGACCATCAGTGGAGTCCAGGCAGAAGAC
241 ------------+---------+---------+---------+---------+---------+  300
    AGACCGAGGTCGAGTCCCTGTTGTCAGTGCAACTGGTAGTCACCTCAGGTCCGTCTTCTG
```
a:  SerGlySerSerSerGlyThrThrValThrLeuThrIleSerGlyValGlnAlaGluAsp   -

```
    GAGGCTGACTATTATTGTCAATCAGCAGACAACAGTGGTGCTTACCCTTTGTTCTTCGGC
301 ------------+---------+---------+---------+---------+---------+  360
    CTCCGACTGATAATAACAGTTAGTCGTCTGTTGTCACCACGAATGGGAAACAAGAAGCCG
```
a:  GluAlaAspTyrTyrCysGlnSerAlaAspAsnSerGlyAlaTyrProLeuPhePheGly   -

```
    GGTGGGACCAAGCTGACCGTCCTACGTCAGCCCAAGGCTGCCCCCTCGGTCACTCTGTTC
361 ------------+---------+---------+---------+---------+---------+  420
    CCACCCTGGTTCGACTGGCAGGATGCAGTCGGGTTCCGACGGGGGAGCCAGTGAGACAAG
```
a:  GlyGlyThrLysLeuThrValLeuArgGlnProLysAlaAlaProSerValThrLeuPhe   -

```
    CCGCCCTCCTC
421 --------+-  431
    GGCGGGAGGAG
```
a:  ProProSer   -

```
      ATGGACATACTTTGTACCACGCTCCTGCTGCTGACCATCCCTTCATGGGTCTTGTCCCAG
    1 ---------+---------+---------+---------+---------+---------+  60
      TACCTGTATGAAACATGGTGCGAGGACGACGACTGGTAGGGAAGTACCCAGAACAGGGTC a:    MetAspIleLeuCysThrThrLeuLeuLeuLeuThrIleProSerTrpValLeuSerGln   -

ATCACCTTGAAGGAGTCTGGTCCTACGCTAGTGAAACCCACACAGACCCTCACACTGACC
   61 ---------+---------+---------+---------+---------+---------+ 120
      TAGTGGAACTTCCTCAGACCAGGATGCGATCACTTTGGGTGTGTCTGGGAGTGTGACTGG a:    IleThrLeuLysGluSerGlyProThrLeuValLysProThrGlnThrLeuThrLeuThr   -

TGCACCTTCTCTGGGTTCTCGCTCAGTACTAGTGGAGTGGGTGTGGCCTGGATCCGTCAG
  121 ---------+---------+---------+---------+---------+---------+ 180
      ACGTGGAAGAGACCCAAGAGCGAGTCATGATCACCTCACCCACACCGGACCTAGGCAGTC a:    CysThrPheSerGlyPheSerLeuSerThrSerGlyValGlyValAlaTrpIleArgGln   -

CCCCCAGGAAAGGCCCTGGAGTGGCTTGCACTCATTTATTGGGATGATGATAAGCGCTAC
  181 ---------+---------+---------+---------+---------+---------+ 240
      GGGGGTCCTTTCCGGGACCTCACCGAACGTGAGTAAATAACCCTACTACTATTCGCGATG a:    ProProGlyLysAlaLeuGluTrpLeuAlaLeuIleTyrTrpAspAspAspLysArgTyr   -

AACCCAACTCTGAACAGCAGGCTCACCATCGCCCAGGACACCGCCAAGAACCAGGTGGTC
  241 ---------+---------+---------+---------+---------+---------+ 300
      TTGGGTTGAGACTTGTCGTCCGAGTGGTAGCGGGTCCTGTGGCGGTTCTTGGTCCACCAG a:    AsnProThrLeuAsnSerArgLeuThrIleAlaGlnAspThrAlaLysAsnGlnValVal   -

CTTACAATGACCAACATGGACCCTGTGGACACAGGCACATATTACTGTGCACACTTAGGT
  301 ---------+---------+---------+---------+---------+---------+ 360
      GAATGTTACTGGTTGTACCTGGGACACCTGTGTCCGTGTATAATGACACGTGTGAATCCA a:    LeuThrMetThrAsnMetAspProValAspThrGlyThrTyrTyrCysAlaHisLeuGly   -

GGATATGATGGCTACGATTTCGCTGACAACTGGGGCCAGGGAATCCTGGTCACCGTCGCC
  361 ---------+---------+---------+---------+---------+---------+ 420
      CCTATACTACCGATGCTAAAGCGACTGTTGACCCCGGTCCCTTAGGACCAGTGGCAGCGG a:    GlyTyrAspGlyTyrAspPheAlaAspAsnTrpGlyGlnGlyIleLeuValThrValAla   -

TCN
  421 --- 423
      AGN a:    Ser   -
```

HETEROHYBRIDOMAS PRODUCING HUMAN MONOCLONAL ANTIBODIES TO HIV-1

CROSS-REFERENCE TO RELATED APPLICATIONS

This application is a continuation of application Ser. No. 07/872,675, filed Apr. 23, 1992, now abandoned, which is a continuation-in-part of application Ser. No. 07/538,451, filed Jun. 15, 1990, now abandoned, and a continuation-in-part of application Ser. No. 07/684,090, filed Apr. 12, 1991, now abandoned, which is a continuation-in-part of application Ser. No. 07/538,451, filed Jun. 15, 1990, now abandoned. The entire contents of both said applications Ser. Nos. 07/684,090 and 07/538,451 are hereby incorporated herein by reference.

This invention was funded in part by a research contract from the National Institute of Allergy and Infectious Disease, National Institutes of Health, No. AI72658 and AI32424, by an award from the Center for AIDS Research (AI 27742) and by the Department of Veteran Affairs, which provides to the United States Government certain rights in this invention.

BACKGROUND OF THE INVENTION

1. Field of the Invention

The present invention in the fields of immunology and virology relates to monoclonal antibodies specifically directed to HIV-1 neutralizing epitopes, and particularly human monoclonal antibodies, lymphoblastoid and heterohybridoma cell lines which produce such antibodies, and methods for producing the human monoclonal antibodies and the lymphoblastoid and heterohybridoma cell lines.

2. Description of the Background Art

The human immunodeficiency viruses (HIV) have been implicated as the causative agent of acquired immune deficiency syndrome (AIDS). Two different HIV families have been identified to date: HIV-1 and HIV-2. It is currently believed that the majority of individuals that become infected with HIV eventually will develop AIDS and are likely to succumb to fatal infections and/or malignancies. Currently, it is estimated that approximately 1.5 million persons have been infected by HIV in the United States alone. Thus, treatment and prevention of HIV infection is among the leading public health challenges today. There is no known cure for HIV infection, which invariably progresses to AIDS and subsequently to the death of the infected individual.

Immunotherapeutic approaches to AIDS have been largely limited to vaccination. Vaccine therapy has relied upon virion proteins, expressed by infected cells, that are designated inter alia as p24, gp41, gp120, etc. (See, for example, Essex, U.S. Pat. No. 4,725,6569.) A number of candidate HIV vaccines, including those involving recombinant HIV antigens, have been prepared and tested, but none has yet proven to be of clinical significance (Berman, P. W. et al., *Nature* 345:622–625 (1990); Girard, M. et al., *Proc. Natl. Acad. Sci. USA* 88:542–546 (1991); Berzofsky, J. A. *FASEB J.* 5:2412–2418 (1991)).

Several studies have demonstrated that effective protection against HIV-1 and HIV-2 infection can be achieved by passive immunization. Initially, two studies showed that immunoglobulin preparations from infected chimps or from infected humans could protect from infection with the HTLV-IIIB isolate of HIV-1 (Emini, E. A. et al., *J. Virol.* 64:3674 (1990); Prince, A. M. et al., *AIDS Res. Hum. Retrovir.* 7:971 (1991)). Subsequently, a mouse monoclonal antibody (mAb) against the V3$_{IIIB}$ loop of gp120, was shown to prevent chimpanzee infection with a homologous strain of HIV-1 (Emini et al., supra). The same mAb, after molecular manipulation to replace the mouse constant regions with human constant regions, could also protect chimpanzees against infection when the mAb was administered before exposure and even 10 minutes after virus challenge (Emini et al., supra). Additionally, serum from vaccinated macaques protected other macaques from subsequent challenge with HIV-2/SIV (Putkonen, P. et al., *Nature* 352:436 (1991)). Studies of active immunization also suggest that neutralizing antibodies to the third variable region (V3) of the HIV-1 envelope glycoprotein, gp120, may prevent infection of chimpanzees (Berman, P. et al., *Nature* 345:622 (1990) and Girard, M., *Proc. Natl. Acad. Sci. USA* 88:542 (1991)).

The use of mAbs for treatment of HIV-1 infections has been hampered because most mAbs directed against HIV-1 proteins currently available in therapeutic quantities are of rodent origin. Administration of non-human antibodies to humans can cause dangerous and even life-threatening immunologic reactions. In addition, such rodent mAbs may not be as effective in interacting with human effector cells or effector molecules (such as the complement system).

Stable human cell lines producing HIV-1-specific mAbs, and the mAb products directed against HIV-1 components, are useful for treating and/or diagnosing individuals infected with this virus. However, human mAbs in general, and those directed against HIV in particular, have proven to be extremely difficult to produce.

Among the explanations for this difficulty are:

(a) The most readily available source of lymphocytes from humans, the peripheral blood, normally contains few antibody-producing cells and, in some instances, none at all;

(b) transformation of antibody-producing cells can be achieved using Epstein-Barr virus (EBV), but production is often unstable and the level of antibody produced is often low;

(c) whereas the level and the stability of antibody production can be enhanced by fusion of EBV-transformed human B lymphocyte lines to mouse myeloma cells, such hybrids (called "heteromyelomas") readily lose human chromosomes, and ultimately antibody production as well; and (d) whereas fusion of normal or transformed B cells to human lymphoblastoid lines or to heteromyelomas can stabilize antibody production, few satisfactory parent lines of this cell type have been available.

Neutralizing antibodies are considered to be essential for protection against viral infection. For this reason, any synthetic vaccine against HIV-1 must include epitopes which induce neutralizing antibodies. Analysis of the reactivity patterns of sera of HIV-infected subjects has revealed that two major types of neutralizing antibodies are elicited by HIV infection. One is directed against the third hypervariable domain (V3) of gp120, and the other against a conserved region of gp120, involved its binding to CD4 (the CD4-binding domain, CD4bd). Antibodies to the V3 loop had been considered to be strain-specific because they appeared to be reactive with only the eliciting strain of HIV (Rusche, J. R. et al., *Proc. Natl. Acad. Sci. USA* 85:3198 (1988)). It has recently been shown that some anti-V3 antibodies can react with more than one viral strain when the amino acid sequence recognized by the antibody is present in both strains (Javaherian, K. et al., Science 250:1590 (1990)). Antibodies against V3 occur in the early phase of infection, but their protective role may decrease in the course of disease due to the emergence of resistant mutants (Nara, P. et al., *J. Virol.* 64:3779 (1990)).

Antibodies to the CD-4 binding site are observed in later phases of infection and, because they recognize a conserved region, they may neutralize many (but not all) strains of HIV and thus be "group-specific" (Ho, D. D. et al., *J. Virol.* 65:489 (1991)). However, anti-V3 antibodies appear to be more potent than antibodies to the CD4bd in terms of their ability to neutralize the virus (Kang, C. et al., *Proc. Natl. Acad. Sci. USA* 88:6171 (1991)).

The V3 neutralizing epitope of HIV-1 is located between two cysteine residues which participate in an intrachain disulfide bond which is predicted to form a hairpin loop structure in the protein. The "tip" of the loop consists of a sequence of four amino acids, Gly-Pro-Gly-Arg (G-P-G-R) (amino acids 315–318 of the V3 loop of the MN isolate residues 15–18 of (SEQ ID NO:1)) that is essentially conserved in North American and European virus isolates (Goudsmit, J., et al., *Proc. Natl. Acad. Sci. USA* 85:4478 (1988); LaRosa, G. J., et al., *Science* 249:932 (1990)) and is flanked by amino acids which differ between various HIV-1 isolates. The V3 loop of gp120 has been shown to be important for biological activity of the virus, including infectivity.

Therapeutic use of anti-HIV antibodies has been proposed (Jackson, G. G, *Lancet* ii:647 (1988); Chanh, T. C. et al., *EMBO J.* 5:3065 (1986); Karpas, A. et al., *Proc. Natl. Acad. Sci. USA* 85:9234 (1988)).

A number of approaches have been taken to preparing antibodies against HIV. For example, Putney et al. (European Patent Publication EP311228) disclosed DNA and proteins useful in assays for detecting and quantifying antibodies against HIV. Putney et al. (European Patent Publication EP255190) disclosed recombinant DNA transfer vectors which comprise all or part of the nucleotide sequence, the translated regions of which encode various fragments of the envelope protein. These protein fragments were said to be useful in immunoassays for detection of HIV antibodies, as antigenic components of AIDS vaccines, and for stimulation of lymphocyte proliferative responses in infected individuals.

Wang (European Patent Publication EP328403) disclosed peptides specifically immunoreactive with antibodies to HIV-1 which neutralize antibodies to HIV-gp120. The disclosed peptides comprise 15–40 amino acids in a sequence corresponding to a region in HIV gp120 which are peptide 126, peptide 127, and analogues thereof. These peptides are used as solid phase immunoadsorbents for detection of antibodies to HIV gp120, including neutralizing antibodies.

Goudsmit et al. (European Patent Publication EP311219) disclosed oligopeptides of 8–17 amino acids in a sequence corresponding to the variable region (V3) in the gp120 protein. Also disclosed are antibodies to the oligopeptides. The oligopeptides comprise the β-turn amino acid sequence GPG or GPGR at positions 312–314 or 312–315 of the IIIB isolate residues 10–12 or 10–13 of (SEQ ID NO:2), and flanking amino acid sequences having a length of at least 1 and preferably at least 2 amino acids and variations in which the GPG or GPGR sequence has been replaced by a different β-turn sequence, and variations in which the free amino group of the N-terminal amino acid and/or the free carboxyl group of the C-terminal amino acid has been blocked or otherwise modified. This document also discusses antibodies to these oligopeptides.

Rusche et al. (European Patent Publication EP306219) disclosed HIV-1 proteins or peptides and DNA sequences coding therefor. These proteins and peptides were said to be useful in the diagnosis, prophylaxis, and therapy of AIDS, in the preparation of HIV vaccines, and for stimulation of lymphocyte proliferative responses in HIV-infected humans.

Petteway et al. (PCT Publication WO 8805824) disclosed a method for producing and selecting a hybridoma cell which produces a mAb to a viral glycoprotein, such as an HIV glycoprotein. The method is said to be useful for obtaining mAbs to HIV proteins such as gp120 and gp41.

Kennedy et al. (European Patent Publication EP245362) disclosed a synthetic peptide which induced an immune response to the virus causing AIDS and ARC. This peptide has a sequence homologous to a portion of the amino acid sequence of the gp120 or gp41 envelope glycoproteins of HIV. The peptides are said to be useful to vaccinate against viral causative agents of AIDS and in diagnostic assays for AIDS.

Grunow et al., (*J. Immunol. Meth.* 106:257–265 (1988)) described the construction a heteromyeloma cell line designated CB-57 by fusing normal human B lymphocytes and a murine myeloma. This heteromyeloma was then used for fusion with EBV-transformed B cells to obtain three cloned heterohybridomas which showed about 30-fold enhanced secretion of IgM antibodies relative to the EBV-transformed parent line. CB-57 cells were also fused with PBL from HIV seropositive individuals, resulting in four heterohybridomas producing IgM anti-p25 antibodies or $IgG_1$ antibodies to p25 or gp41. No anti-gp120 heterohybridomas were reported. A later report from the same group (Berzow, D. et al., *Proc. IVth Int'l. AIDS Conf.*, Montreal, 1989, abstr. TCP 150) indicated that one clone was capable of continuous production of antibodies to gp120, but no data were available on the activity of this antibody.

Scott, C. F. et al. (*Proc. Natl. Acad. Sci. USA* 87:8597–8601 (1990 Nov.)) disclosed a human $IgG_1$ mAb termed N701.9b which was derived from EBV-transformed B cells of an HIV-infected donor. This antibody recognized the principal neutralizing domain within the V3 loop of MN-like strains, more particularly an epitope containing at least 7 amino acids in positions 316–322. This antibody had neutralizing activity for MN but not IIIB or RF strains of HIV-1. This antibody was therefore of the "type-specific" variety, in stark contrast to some of the monoclonal antibodies of the present invention which have broad reactivity against diverse HIV-1 strains.

A broadly neutralizing murine mAb NM-01 that recognizes the V3 loop (residues 312–326) of HIV-1 was disclosed by Ohno, T. et al. (*Proc. Natl. Acad. Sci. USA* 88:10726–10729 (1991 Dec.)). This antibody could neutralize both MN and IIIB strains and reacted equally with loop peptides from MN, IIIB, RF and CDC4 isolates. This antibody reacted less well, or not at all, with loop peptides from NY5, Z2, Z6 and ELI isolates. The authors concluded that this broad reactivity was due to recognition of the GPGR sequence (residues 15–18 of SEQ ID NO:1). This murine antibody is clearly distinct from the human mAbs disclosed in the present application and is highly limited in its clinical utility.

Other murine mAbs which are broadly reactive to some extent are described in Åkerblom, L. et al., AIDS, 4:953–960 (1990). The neutralizing capacity of such mAbs appeared to be limited to a sequence QRGPGR (residues 10–15 of SEQ ID NO:2) of the HTLV-IIIβ strain.

SUMMARY OF THE INVENTION

It is an object of the present invention to overcome the aforementioned deficiencies in the prior art.

It is another object of the present invention to provide a molecule which is broadly reactive with the V3 loop of the gp120 glycoprotein of various strains of HIV-1.

It is a further object of the present invention to provide a molecule which broadly neutralizes many different strains of HIV-1.

It is another object of the present invention to provide a molecule which neutralizes both the MN isolate and the IIIB isolate of HIV-1.

It is yet another object of the present invention to provide a molecule which neutralizes all of the MN, AL-1, SF-2, DU 6587-5 and WMJ-2 isolates of HIV-1.

It is still a further object of the present invention to provide a molecule which is capable of neutralizing all of the isolates of HIV-1 previously mentioned, as well as the RF isolate of HIV-1.

It is yet another object of the present invention to provide such a molecule which is an antibody and preferably a human monoclonal antibody.

It is still a further object of the present invention to provide an antibody, or a molecule including the antigen binding portion of an antibody, whose binding epitope is GPGR (residues 15–18 of SEQ ID NO:1).

It is yet a further object of the present invention to provide an antibody, or a molecule including the antigen binding portion of an antibody, whose binding epitope is GRAF (residues 17–20 of SEQ ID NO:1).

It is another object of the present invention to provide DNA encoding such molecules and cell lines which produce such molecules, particularly cell lines which produce antibodies having such properties and most particularly human-mouse heterohybridoma cell lines for producing human monoclonal antibodies having such properties.

It is still a further object of the present invention to provide methods for producing such heterohybridoma cells and for producing such antibodies.

These and other objects of the present invention will be better understood upon consideration of the following brief description of the drawings and detailed description of preferred embodiments.

BRIEF DESCRIPTION OF THE DRAWINGS

FIG. 5 is a graphical representation of the mAb mapped epitopes to the V3 loop of $HIV_{MN}$ (SEQ ID NO:1). The loops are presented in order: from the shortest sequence of 4 residues to the longest with seven. The epitopes of the mAbs 381/95-D and 412-D have not been determined yet, but the mAbs have been shown to bind to the 15-mer peptide.

FIG. 6A: Neutralization of $HIV_{MN}$ incubated with 257-D in the absence of complement for 1 hr.

FIG. 8 is a graph showing a scan of ELISA reactivity of human mAb 447-D (□) and 694-D (■) with overlapping hexapeptides or heptapeptides, respectively, with sequences corresponding to residues 306–328 of the gp120$_{MN}$ envelope (residues 6–28 of SEQ ID NO:1). The reactivity of each hexapeptide or heptapeptide with heterohybridoma supernatants is shown on the ordinate (O.D. is optical density or absorbance at 410 nm). Each hexapeptide or heptapeptide is designated by the single letter code of its N-terminal residue and the subsequent 5 or 6 amino acids. The entire abscissa represents the sequence of 306–328.

FIGS. 9A through 9F are for substitutions at H, I, G, P, G and R respectively. Results are shown as O.D. (optical density, or absorbance at 410 nm) in arbitrary units.

FIG. 10 shows the DNA (SEQ ID NO:3) and corresponding amino acid sequence (SEQ ID NO:4) of the light chain of the variable domain of mAb 447-D.

FIG. 11 shows the DNA (SEQ ID NO:5) and corresponding amino acid sequence (SEQ ID NO:6) of the heavy chain of the variable domain of mAb 447-D.

FIG. 12 shows the DNA (SEQ ID NO:7) and corresponding amino acid sequence (SEQ ID NO:8) of the light chain of the variable domain of mAb 694-D.

FIG. 13 shows the DNA (SEQ ID NO:9) and corresponding amino acid sequence (SEQ ID NO:10) of the heavy chain of the variable domain of mAb 694-D.

DESCRIPTION OF THE PREFERRED EMBODIMENTS

Figure 1:
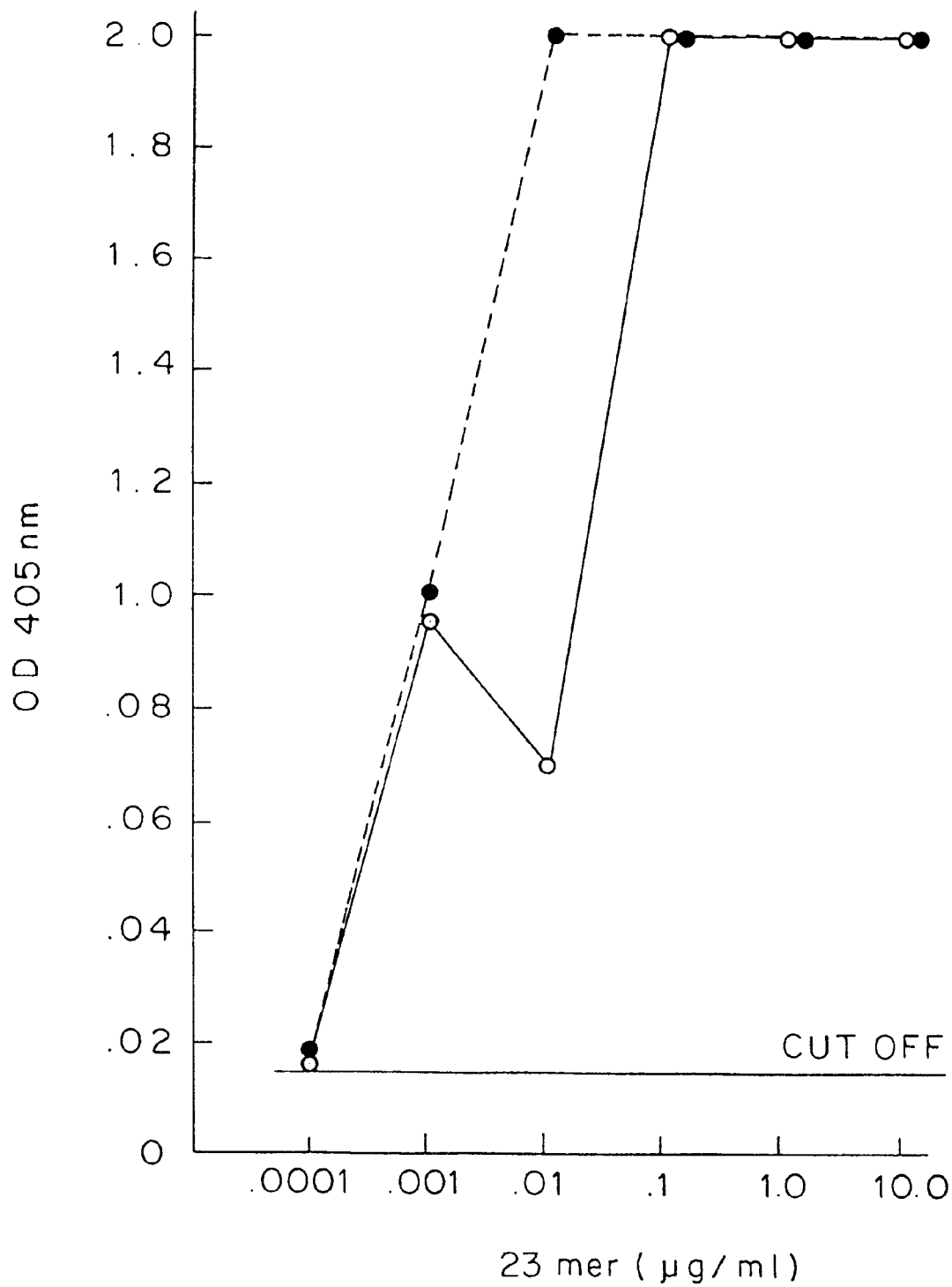
FIG. 1 is a graph showing the immune reactivity of 257-D (●) and 268-D (○) to the 23-mer HIV-1 synthetic peptide in an antigen-limited ELISA.

Cell lines making human IgG mAb to a neutralizing epitope of HIV-1, such as epitopes associated with the gp120 glycoprotein, are produced by EBV transformation of human peripheral blood mononuclear cells followed by selection of cell lines making antibody of the desired specificity, followed by fusion of the selected EBV-transformed cells to a heteromyeloma cell line. The resultant heterohybridoma cells each make a human mAb having the epitope-specificity (e.g., for the gp120 epitope) of the antibodies produced by the selected parent EBV-transformed cells. In the EBV transformation technique of the present invention, unfractionated peripheral blood mononuclear cells, not just B cells, are incubated with EBV.

An important advantage of the present invention is the screening technique for selecting an EBV-transformed lymphocyte line which makes the antibody of desired specificity. First, the screening method utilizes synthetic or recombinant peptides representing the epitope or epitopes of interest, rather than crude viral preparations. Furthermore, this intense screening procedure is performed at an earlier stage of the development process than is common in the prior art. This combination of early and highly rigorous screening of antibody-producing EBV-transformed lymphocytes avoids disadvantages accompanying the unnecessary production and testing of many cell lines which make undesired antibodies of broad or questionable specificity. The invention is also directed to methods in which these selected EBV-transformed, antibody-producing, cell lines are fused with mouse-human heteromyelomas followed at an early time by cloning, resulting in selection of heterohybridoma cell lines which are more stable and produce greater amounts of antibody than known heretofore.

The gp120 glycoprotein, which contains one or more neutralizing epitopes recognized by the cells and antibodies of the present invention, may be derived from any of the known HIV-1 strains, such as the relatively common MN strain.

By the term "heteromyeloma" is intended a hybrid cell produced by fusion of a non-human myeloma cell line and a human myeloma cell line. Typically, a mouse myeloma or plasmacytoma cell is the fusion partner of the human myeloma cell. Such non-human and human myeloma and heteromyeloma cell lines are well-known in the art and are exemplified by cell lines reported in Teng, N. N. et al., *Proc. Natl. Acad. Sci. USA* 80:7308 (1983); Kozbor, D. et al., *Hybridoma* 2:7 (1983); and Grunow, R. et al., *J.Immunol. Meth.* 106:257–265 (1988).

As intended in the present invention, heteromyeloma cells are used as fusion partners for selected EBV-transformed human cells to produce the heterohybridomas of this invention.

In a preferred embodiment, the heteromyeloma SHM-D33 is used as a fusion partner. This cell line is available from the ATCC, under accession number ATCC CRL1668.

The term "heterohybridoma", as used herein, refers to a hybrid cell line produced by fusion of an antibody-producing cell of one species with a heteromyeloma. The term "heterohybridoma" has also been used elsewhere to refer to any interspecies hybridoma, such as one resulting from the fusion of an antibody-producing human lymphocytoid cell line cell and a murine myeloma cell. However, the term as used herein is more narrowly defined.

In one embodiment of this invention, a human antibody-producing cell is fused with a mouse-human heteromyeloma. In a preferred embodiment, the heterohybridoma is the result of fusing an EBV-transformed human lymphocyte which is producing an antibody to a neutralizing epitope of HIV, with a human-mouse heteromyeloma. In a more preferred embodiment, the human-mouse heteromyeloma is the cell line designated as SHMD33.

By the term "neutralizing epitope" is intended an epitope which, when bound by an antibody specific for this epitope, results in neutralization of the virus. Neutralization of any biological activity of the virus, such as, for example, syncytium formation or infectivity, falls within the scope of "neutralization", as used herein.

To generate human mAbs against a neutralizing epitope of HIV-1 gp120, human peripheral blood lymphocytes are transformed by EBV, as described, for example in Gorny, M. K. et al., *Proc. Natl. Acad. Sci. USA* 86:1624–1628 (1989), which is hereby incorporated by reference.

Preferably, the cells to be transformed are derived from the blood of an individual producing anti-HIV-1 antibodies.

The cultures of EBV-transformed cells are screened for antibody to the epitope of interest. In one embodiment the epitope is a neutralizing epitope of the gp120 protein and the screening is performed using purified gp120, a fragment thereof, or a synthetic peptide representing a portion thereof. In a preferred embodiment, cultures are screened for antibody to an epitope of the V3 loop of gp120 using a synthetic 23-mer peptide from the V3 loop representing amino acids 306–328 of gp120$_{MN}$ residues (6–28 of SEQ ID NO:1). In addition to such a peptide, additional peptides having at least 6 amino acids are useful for screening the EBV-transformed cells in order to identify antibody producing cells of the desired epitope specificity.

Any of a number of immunoassays well known in the art can be used for this screening process. A preferred immunoassay is an Enzyme Linked Immunosorbent Assay, or ELISA. Using such an assay, the culture supernatants are tested for the presence of antibodies of desired specificity and isotype.

Positive EBV-transformed cultures are cloned repeatedly by any of a number of cloning methods known in the art, such as, for example, by doubling dilution. Cells from cultures found to be positive for the desired antibody specificity are also fused with cells of the heteromyeloma line to produce a heterohybridoma. Fused cells are subsequently cloned by culturing at a density of about 1–100 cells per well.

Specificity of the antibody produced by the heterohybridoma is determined by immunoassay methods which are well known in the art. In a preferred embodiment, ELISA and radioimmunoprecipitation (RIP) procedures are used. The antigen preparation comprises HIV-1 virions (such as strain MN), lysates of viruses or of infected cells, such as MN and HTLV-IIIB lysates, viral proteins such as gp120, or recombinant or synthetic viral peptides such as the 23-mer described above.

The mAbs of the present invention are of the IgG isotypes and may be recovered from the supernatants of the heterohybridoma cell cultures and purified by conventional methods known in the art for purification of IgG. Such methods include, but are not limited to, protein-A Sepharose affinity chromatography, a combination of Affigel Blue (BioRad, Richmond, Calif.) and Protein-A Sepharose chromatography, or High Performance Liquid Chromatography.

Preferred human mAbs according to the present invention are those which are neutralizing and "broadly reactive." As used herein, the term "broadly reactive" is defined as recognizing at least two divergent HIV-1 isolates or strains. Thus, an antibody that recognizes the V3 loop of gp120 of the MN family of viruses (such as the AL-1, SF-2, DU-6587-5, DU 7887-7, and WMJ-2) and the IIIB isolate and neutralizes these viruses is considered to be broadly reactive as intended herein. An antibody that recognizes and neutralizes viruses of the MN family and the RF strain is broadly reactive as intended herein. Preferred broadly reactive antibodies recognize an epitope of the V3 region having the amino acid sequence GPXR (SEQ ID NO:11) (where X can be any amino acid) or GRAF (residues 17–20 of SEQ ID NO:1), i.e., they will recognize or bind to the V3 loop of gp120 when such amino acid sequences are present with a wide variety of other amino acids in the V3 region. Most preferred examples of broadly reactive neutralizing antibodies, produced by heterohybridoma cells of the present invention, are 447-D and 694-D, described in more detail in the Examples below.

As used herein, the term that an antibody or compound recognizes an epitope of the V3 region having a particular specified amino acid sequence, such as GPXR (SEQ ID NO:11) or GRAF (residues 17–20 of SEQ ID NO:1) means that the antibody or compound will recognize or bind to the V3 loop of gp120 when such amino acid sequence is present with a wide variety of other amino acids in the V3 region. Thus, the binding ability of the antibody or compound is substantially independent of the amino acid sequences (other than the specified sequence) which may be present in the V3 loop region of gp120. Thus, unlike prior art antibodies, the antibody of the present invention will bind to the V3 region of gp120 provided that such region includes the specified sequence without requiring that any specific amino acids be present in the portion of the loop region immediately adjacent to the specified sequence. Thus, the antibody reacts with a wide variety of HIV strains in that GPXR and GRAF are believed to be conserved in the V3 region of gp120, i.e., a major proportion of HIV strains has GPXR and/or GRAF in the V3 region thereof. In contrast, such major proportions of HIV strains vary in the remaining amino acids which are present in the V3 region. As a result, if an antibody requires an epitope that includes amino acids in addition to the GPXR or GRAF sequence, or requires a variation of the GPXR or GRAF sequence, such antibodies will not bind to a major proportion of the HIV strains in that an epitope requiring additional amino acids or alternative amino acids is not "conserved" in the V3 region.

The broadly reactive neutralizing human mAbs of the present invention are distinguishable from antibodies of the prior art (Scott et al., supra) in HIV strains recognize diverse HIV strains or isolates. They are distinguishable from broadly reactive neutralizing murine mAbs specific for the V3 loop of gp120 (Ohno et al., supra, and Åkerblom, supra) in that they are of human origin and therefore of much greater therapeutic utility. They are also even more broadly reactive than the murine mAbs of Ohno or Åkerblom.

When administered to humans infected with HIV-1, or at risk for HIV infections, the antibodies of the present invention can provide therapeutic or prophylactic benefits. Such individuals particularly at risk are known in the art and include health care workers who have been inadvertently exposed to HIV-1. Most preferable are the human mAbs which are broadly reactive against diverse HIV-1 strains, i.e., the 447-D and 694-D antibodies.

The antibodies of the present invention are also useful in diagnostic assays of the type used to determine if a patient has been exposed to, or infected with, HIV-1.

The antibodies are also useful for analyzing the expression of HIV proteins or peptides for which they are specific.

The HIV-specific human mAbs of the present invention can be used to treat individuals infected by HIV or suffering from AIDS. The antibodies according to the invention are administered parenterally or enterally by any of a number of known routes. For example, administration may be subcutaneous, intravenous, intramuscular, intraperitoneal, transdermal, or intrathecal. Alternatively, or concurrently, administration may be by the oral, vaginal or rectal route. The antibodies may also be administered into the amniotic cavity for in utero treatment. The preferred routes are intravenous and intramuscular.

The dosage of antibody administered will be dependent upon the age, health, and weight of the recipient, kind of concurrent treatment, if any, frequency of treatment, and the nature of the effect desired. Effective amounts of the mAbs are from about 0.1 to about 4000 mg per dose, and preferably from about 3 to about 35 mg/kg per dose. Treatment may require infusion or injection of the antibody daily, weekly, monthly, etc., over a period of days, weeks, months, or even years, as would be readily ascertained by one of skill in the art. It is expected that the preferred schedule will be once every two weeks for 1–3 months.

A typical treatment regimen comprises administration of an effective amount of antibody administered over between one week and about six months. Duration of treatment required to achieve a therapeutic result will vary from patient to patient, depending upon the severity and stage of the illness and the individual characteristics of each patient.

The total dose required for each treatment may be administered by multiple doses or in a single dose. The mAbs may be administered alone or in conjunction with other therapeutics directed to HIV-1 infection, such as AZT, or directed to other disease symptoms.

The mAbs of the present invention can be administered to HIV-infected expectant mothers. Since the antibodies of the present invention are of the IgG isotype, they can cross the placenta and reach the fetus. This may prevent infection of the fetus or, alternatively, provide effective therapy for an infected fetus.

Pharmaceutical compositions comprising the antibodies of the invention include all compositions wherein the antibody is contained in an amount effective to achieve its intended purpose. In addition to the antibody, the pharmaceutical compositions may contain suitable pharmaceutically acceptable carriers comprising excipients and auxiliaries which facilitate processing of the active compounds into preparations which can be used pharmaceutically. An additional pharmaceutical composition within the scope of the present invention is a combination of the antibody of the invention with an intravenous immunoglobulin preparation as is known in the art.

Pharmaceutical compositions include suitable solutions for administration by injection or orally, and contain from about 0.01 to 99 percent, preferably from about 20 to 75 percent of active component (i.e. the antibody) together with the excipient. Pharmaceutical compositions for oral administration include tablets and capsules. Compositions which can be administered rectally include suppositories. Compositions which can be administered vaginally include creams and gels.

The mAbs of the present invention can be conjugated to cytotoxic agents and used as immunotoxins (see, for example, Vitetta et al., Science 238:1098–1104 (1987)), or incorporated onto the surface of liposomes containing anti-HIV drugs or toxins to specifically target such drugs or toxins to infected cells. As used herein, the term "immunotoxin" refers to a conjugate or construct of an antibody with one or more toxins, drugs, radionuclides, or cytotoxic agents. A toxic moiety can either be chemically conjugated to the antibody of the invention, or alternatively, can be ligated through recombinant DNA technology. In such a ligation, the DNA encoding the toxic protein or an active fragment thereof is ligated to the DNA encoding the entire, or a portion of, the mAb heavy chain, light chain, or both. Such genetic constructs and methods for making them are known in the art. Among the toxins that may be conjugated to the antibodies of the present invention are ricin, diphtheria toxin, Pseudomonas toxin, tumor necrosis factor-alpha, and others known in the art.

In a typical treatment using the mAbs of the present invention as immunotoxins, the antibody is conjugated to a toxin such as ricin that, alone, is toxic to HIV-infected as well as uninfected cells. By coupling the cytotoxic agent to the antibody, a high level of toxic efficacy can be achieved in a highly localized manner, against the target cell to which the antibody has delivered the toxin, with a sparing of neighboring infected cells to which the antibody did not bind.

While the description of the utility of the antibodies of the present invention has referred to intact antibodies, preferably human monoclonal antibodies, it should be understood that it is the epitope binding site of the antibody which provides the desired function. Thus, besides the intact antibody, proteolytic fragments thereof such as the Fab or F(ab')$_2$ fragments can be used. Furthermore, the DNA encoding the variable region of the antibody can be inserted into other antibodies to produce chimeric antibodies (see, for example, U.S. Pat. No. 4,816,567) or into T-cell receptors to produce T-cells with the same broad specificity (see Eshhar, Z. et al., Br. J. Cancer Suppl., 10:27–9 (1990); Gross, G. et al., Proc. Natl. Acad. Sci. USA, 86:10024–8 (1989)). Single chain antibodies can also be produced and used. Single chain antibodies can be single chain composite polypeptides having antigen binding capabilities and comprising a pair of amino acid sequences homologous or analogous to the variable regions of an. immunoglobulin light and heavy chain (linked $V_H$-$V_L$ or single chain $F_V$). Both $V_H$ and $V_L$ may copy natural monoclonal antibody sequences or one or both of the chains may comprise a CDR-FR construct of the type described in U.S. Pat. No. 5,091,513 (the entire contents of which are hereby incorporated herein by reference). The separate polypeptides analogous to the variable regions of the light and heavy chains are held together by a polypeptide linker. Methods of production of such single chain antibodies, particularly where the DNA encoding the polypeptide structures of the $V_H$ and $V_L$ chains are known, may be accomplished in accordance with the methods described, for example, in U.S. Pat. Nos. 4,946,778, 5,091, 513 and 5,096,815, the entire contents of each of which are hereby incorporated herein by reference.

When used in the present specification and claims, the recitation "a molecule including the antigen-binding portion of an antibody" is intended to include not only intact immunoglobulin molecules of any isotype and generated by any animal cell line or microorganism, but also the reactive fraction thereof including, but not limited to, the Fab fragment, the Fab' fragment, the F(ab')$_2$ fragment, the variable portion of the heavy and/or light chains thereof, and chimeric or single-chain antibodies incorporating such reactive fraction, as well as any other type of molecule or cell in which such antibody reactive fraction has been physically inserted, such as a chimeric T-cell receptor or a T-cell having such a receptor, or molecules developed to deliver therapeutic moieties by means of a portion of the molecule containing such a reactive fraction.

Having now generally described the invention, the same will be more readily understood through reference to the following examples which are provided by way of illustration, and are not intended to be limiting of the present invention, unless specified.

EXAMPLE I

Production of Human Heterohybridomas Generating Human Monoclonal Antibodies to HIV-1

The objective of this study was to examine optimal conditions for establishing cell lines producing human mAbs against HIV-1.

METHODS

Peripheral blood lymphocytes derived from 74 HIV seropositive individuals were transformed with EBV. Cultures producing antibodies to HIV were expanded and cloned several times on irradiated GK5 feeder cells by doubling dilution (5000 to 10 cells/well). Five of the 74 specimens could be processed by both cloning and fusions. Simultaneous with the first cloning (i.e., 5 to 7 weeks after initiation of culture), the lymphoblastoid cells from expanded cultures were fused with heteromyeloma SHM-D33 cells. Anti-HIV positive hybrids were cloned at 100 to 1 cell/well. The specificity of the mAb was tested by ELISA, Western blot and RIP.

RESULTS

The immortalization of PBL by EBV alone gave rise to two cell lines synthesizing human mAbs. However when EBV-transformed cells were fused to SHM-D33, five hybrid lines making human mAb were obtained. All cell lines have been in culture for more than 24 months. The characterization of these cell lines is set forth in Table 1.

TABLE 1

| Patient Code | Stable EBV Lines | Stable Hybrids | Isotype | Specificity |
| --- | --- | --- | --- | --- |
| 167 | None | 167-7-D | IgG$_1$, lambda | gp41 |
| 181 | None | 181-1-D | IgG$_2$, kappa | gp41 |
| 240 | None | 240-1-D | IgG$_1$, kappa | gp41 |
| 238 | 238-2 | 238-2-D | IgG$_1$, lambda | p24 |
| 241 | 241-1 | 241-1-D | IgG$_1$, lambda | p24 |

Conclusion

EBV transformation of blood cells followed by fusion to a heteromyeloma appears to be the most effective method for the generation of human mAb to HIV-1 and is more efficient than EBV transformation alone.

EXAMPLE II

Production of Human Heterohybridomas Generating Human Monoclonal Antibodies to HIV-1

Subjects

A group of 41 asymptomatic HIV-seropositive individuals participated in the study. The presence of serum antibodies to HIV-1 was tested by commercial ELISA (Genetic Systems) and confirmed by Western blot using Novapath Immunoblot Assay (Bio-Rad). The CD4 and CD8 phenotype of lymphocytes from each subject was determined using Leu 3a and Leu 2a antibodies (supplied by Becton-Dickinson) by flow cytometry using a Cytofluorograf II (Ortho). Peripheral blood white blood cell counts were processed by a Coulter Counter and differential counts were performed manually.

Patients were classified as to disease progression using an immunologic staging system such that patients were divided into four categories on the basis of the following, previously described criteria (Zolla-Pazner, S. et al., Proc. Natl. Acad. Sci. USA 84:5404 (1987)):

| Scale Score | CD4:CD8 Ratio | CD4 cells/mm$^3$ | Lymphocytes/mm$^3$ |
|---|---|---|---|
| 0 | >1.0 | >500 | >1500 |
| 1 | <1.0 | >500 | >1500 |
| 2 | <1.0 | <500 | >1500 |
| 3 | <1.0 | <500 | <1500 |

Synthetic Peptide Used for Screening

A peptide which spans 23 amino acids of the gp120 V3 loop of the MN strain of HIV-1 (23-mer peptide) was synthesized by solid-phase methodology (Peninsula Laboratories, Inc. Belmont, Calif.). The peptide has the following sequence (residues 6–28 of SEQ ID NO:1):

YNKRKRIHIGPGRAFYTTKNIIG

This peptide was used in an ELISA assay to screen for antibodies specific to it.

Establishment of EBV-Transformed Cell Lines

The method for producing human cell lines synthesizing mAbs to HIV-1 was described by Gorny et al., 1989, supra. Peripheral blood mononuclear cells were incubated with Epstein-Barr virus (EBV) and cultured for 3–4 weeks in 96-well microplates. After screening for antibodies in the culture supernatants using the 23-mer peptide in an ELISA, cells from cultures having supernatants positive for these antibodies were expanded, subcultured several times, and finally further expanded into flasks. These cells are called lymphoblastoid cells.

Cell Fusion

The heteromyeloma (mouse-human hybrid) SHM-D33 (Teng, N. H. et al., Proc. Natl. Acad. Sci. USA, 80:7308 (1983)) was grown in Iscove's modified Dulbecco's medium supplemented with 15% fetal bovine serum, 2 mM L-glutamine, penicillin (100 units/ml), and streptomycin (100 µg/ml) (complete medium). Periodically, heteromyeloma cells were cultured with the antibiotic G418 at 200 µg/ml to eliminate neomycin-sensitive variants.

Two days prior to fusion, the SHM-D33 cells were cultured at a concentration of 1–2×10$^5$ cells/ml (log phase growth). The viability of the cells, as determined by erythrosin B dye exclusion, exceeded 95%.

The SHM-D33 cells were washed twice in phosphate-buffered saline and then mixed with the lymphoblastoid cells which had been expanded from initial culture but had not yet been cloned. The cells were mixed at a ratio of 1:3 and centrifuged. Then, 1 ml of 50% polyethylene glycol 1300–1600 (Sigma Chemicals) was added dropwise to the pellet over a period of one minute with constant agitation that was continued for another one minute. During the next five minutes, the cells were slowly diluted with Iscove's medium and, after pelleting by centrifugation at 200×g, the cells were gently resuspended in complete medium and plated in 96-well microplates at a concentration of 8×10$^4$ cells/100 µl/well. The next day, 1×10$^4$ mouse peritoneal cells were added per well as feeder cells, and the cultures were continued in the presence of 0.5 mM hypoxanthine, 0.2 µM aminopterin, 16 µM thymidine (HAT) and 1 µM ouabain (Sigma Chemicals). Feeding was repeated twice weekly with fresh complete medium supplemented with HAT. After two to three weeks all culture wells were screened for antibody production against the aforementioned peptide and heterohybrids producing antibodies reactive with the 23-mer peptide were expanded in 24-well plates. Hybrids that produced the highest level of antibodies (and IgG) measured by ELISA were cloned at concentrations of 100, 25, and (at least twice at) 1 cell per well.

Antibody Detection

Culture supernatants were screened against the 23-mer by ELISA as described in Gorny et al., Proc. Natl. Acad. Sci. USA 88:3238 (1991). Immulon 2 plates (Dynatech) were coated overnight at 4° C. with the synthetic peptide (1 µg/ml), diluted in sodium carbonate buffer, pH 9.6. Plates were washed three times and culture supernatants were added to each well and incubated for 90 minutes at 37° C., then washed. Goat anti-human IgG (gamma chain-specific) conjugated to alkaline phosphatase (Zymed Laboratories) was added and incubated for another 90 minutes at 37° C. and washed as above. The substrate, p-nitrophenyl phosphate (Sigma Chemicals), was added for 30 min and the absorbance was read at 405$_{nm}$ on an automated ELISA reader (MR 700 Microplate Reader (Dynatech)).

RESULTS

A total of 46 blood specimens derived from 41 HIV-seropositive individuals were processed and transformed with EBV. After 3 to 4 weeks of culture, an average of 2.9% of the wells were positive for antibody against the 23-mer of the V3 loop as revealed by ELISA. Table 2 shows that the percentage of positive wells was slightly increased in the group of subjects with a scale score of 1, but that there was no significant difference in the yield of positive cultures from patients with different levels of severity of the disease.

TABLE 2

PRODUCTION OF ANTIBODIES SPECIFIC FOR A 23-mer OF THE MN STRAIN gp120 V3 LOOP BY EBV-TRANSFORMED HUMAN LYMPHOCYTES

| Scale Score | # of Cultures | # of Wells | # (%) Positive Wells |
|---|---|---|---|
| 0 | 1 | 610 | 16 (2.6%) |
| 1 | 17 | 4363 | 176 (4.0%) |
| 2 | 21 | 7340 | 171 (2.3%) |
| 3 | 7 | 2880 | 81 (2.8%) |

Lymphoblastoid cells from positive wells were further expanded in 24-well plates and, once per week, fresh culture supernatants were tested for antibody specificity by ELISA using the 23-mer peptide. Two lymphoblastoid cell lines, 257-2 (ATCC #CRL10483) and 268-11 (ATCC #CRL10482), that were producing high levels of specific antibody against the 23-mer were cloned by doubling dilution (from 10,000 to 10 cells per well). Cells from wells plated at the lowest cell density that continued to produce antibodies were further cloned three times at 100 to 10 cells/well.

Simultaneously with the original cloning, both lymphoblastoid cell lines (257-2, 268-11) were fused with heteromyeloma SHM-D33. All wells showed growth of hybrid cells. Three weeks after fusion, 50 of 183 wells (29%) plated with 257-2 heterohybrids and 43 out of 48 wells (90%) plated with 268-11 heterohybrids were found to contain antibody against the 23-mer. From each fusion, the eighteen clones producing the highest concentration of antibody (based on absorbance in ELISA), were expanded in 24-well plates. The production of antibodies was monitored weekly, and cells producing supernatant yielding the highest specific antibody and IgG concentrations were selected for cloning. The heterohybridomas were cloned at 100 and 25 cells/well and subsequently twice at 1 cell/well.

While the lymphoblastoid cell lines 257-2 (ATCC #CRL10483) and 268-11 (ATCC #CRL10482) produced 6.4 and 3.8 $\mu$g IgG/ml/$10^6$ cells/24 hr, respectively, the related heterohybridomas, 257-D (ATCC #HB 10480) and 268-D (ATCC #10481) produced 20.5 and 11.3 $\mu$g IgG/ml/$10^6$ cells/24 hr, respectively. The mAbs were shown to react in ELISA with the 23-mer when the latter was bound to the wells of microtiter plates at concentrations as low as 1 ng/ml (FIG. 1).

EXAMPLE III

Human Heterohybridoma Production Without Prolonged Expansion of EBV-Transformed Lymphocytes The fusion of EBV-transformed cells and heteromyeloma SHM-D33 is usually performed after 2–3 weeks of expansion of EBV immortalized cells in 24-well microplates. This is equivalent to 5–7 weeks after culture initiation. However, the expansion period is very critical for production of the mAb because the majority (at least 90%) of culture wells become negative for mAb production during this period. We therefore tested an alternative method in which the expansion period was excluded and fusion took place 3–4 weeks after culture initiation. Thus, 96-well plates with EBV-transformed cells were screened for reactivity against the 23-mer peptide by ELISA, as described in Example II, 3–4 weeks after culture initiation. Positive cultures were expanded, subcultured and fused with heteromyeloma SHM-D33 as described in Example II. The fused cells were cultured 2–3 weeks in selective medium with mouse peritoneal feeder cells. All cultures were screened for antibody production against the 23-mer peptide. Hybrids producing reactive antibodies were expanded, subcloned several times at 100 or 10 and finally at 1 cell per wll, and then expanded into flasks.

The average number of cell lines obtained secreting an antibody to HIV-1 after EBV transformation followed by early fusion, described in this example, was greater than the number of HIV-seropositive individuals from whom the PBL was derived. On the other hand, an average of only about seven lines per 100 patient specimens were obtained by EBV-transformation or by EBV-transformation and late fusion as described in Examples I and II. Thus, the early fusion of EBV-transformed cells without expansion of positive wells is a more efficient method than previous techniques for the generation of human mAbs to HIV-1.

One hybrid line, 694-D, was produced in an analogous manner except that it was selected using rgp120 $_{IIIB}$ as antigen. This is in contrast to the selection of all of the other lines discussed herein with the 23-mer peptide of V3$_{MN}$ as antigen.

EXAMPLE IV

Methods of Analysis of Human Antibodies

Antibody Characterization

The specificity of antibody binding was assessed by radioimmunoprecipitation (RIP). RIP assays were carried out by the method of Pinter et al. (*J. Immunol. Meth.* 112:735 (1988)) with 30 $\mu$g of HTLV-IIIB lysate (Organon Teknika) and/or MN lysate (Advanced Biotechnologies, Inc.) labelled with $^{125}$I using the Bolton-Hunter reagent (New England Nuclear). Culture supernatants were incubated with labeled viral lysate which remained untreated or was reduced by dithiothreitol and alkylated with iodoacetamide. Fixed *Staphylococcus aureus* (Pansorbin, Calbiochem, San Diego, Calif.) was then added to precipitate the immune complexes. When the isotype of human mAb was IgG3 (which does not bind to Protein A), a murine mAb against human IgG3 was used for precipitation. The immunoprecipitate was further processed for electrophoretic analysis as previously reported by Gorny et al. (1989), supra.

Antibody subclasses, light-chain type of antibody and immunoglobulin quantitation were determined by ELISA as previously described by Gorny et al. (1991), supra.

Antigen-limited ELISA

To discern the patterns of mAb cross-reactivity and estimate relative antibody affinities, ELISAs were performed at limiting antibody concentrations. Immulon 2 plates were coated with decreasing amounts of synthetic peptide at concentrations ranging from 1 $\mu$g/ml to 10 ng/ml. The concentration of mAbs used was standardized to 10 $\mu$g/ml. The mAbs were allowed to incubate with the peptide coated plates and bound antibody was measured as described for the ELISA.

Epitope Mapping

The fine specificity of the mAb was determined using the Epitope Mapping Kit (Cambridge Research Biochemicals, Valley Stream, N.Y.) which utilizes the method developed by Geysen et al. (Geysen, H. M. et al. *Proc. Natl. Acad. Sci. USA* 81:3998–4002 (1984)) to synthesize hexapeptides on plastic pins. Eighteen sequential, overlapping hexapeptides which spanned the 23-mer were synthesized in situ on plastic pins with two additional control peptides. The peptides were deprotected, then washed and dried according to the manufacturer's instructions. Because the configuration of pins fits into 96-well microplates, the ELISA assays were carried out in standard microplates as recommended by the manufacturer. Thus, all peptide-containing pins were allowed to react with culture supernatants from the cell lines being tested at a 1:10 dilution in 0.1% Tween-20 in PBS containing 1% ovalbumin and 1% bovine serum albumin. Thereafter, the pins were washed and reacted with horseradish peroxidase-conjugated goat anti-human IgG. The color reaction was read in a Dynatech MR-700 plate reader as absorbance at 405 nM.

Determination of mAb Affinity

Determination of the absolute dissociation constants ($K_d$) of human mAbs was performed using an ELISA methodology as described by B. Friguet et al., *J. Immunol. Methods* 77:305–319 (1985). Briefly, the culture supernatants were tested at IgG concentrations ranging from 2.5 to 0.5 $\mu$g/ml. The peptides were used at concentrations of $10^{-5}$ to $10^{-8}$M. Supernatants and the relevant peptides at various concentrations were mixed in equal volumes and, after 16 hr, each mixture was added to wells coated with the homologous peptide (1 μg/ml) and the amount of unbound mAb was measured by ELISA. Data were plotted according to the Friguet modification of the Klotz method (Friguet et al., supra) to determine the $K_d$.

Neutralization Assays

To determine biological activity of the monoclonal antibodies of the present invention, four different types of neutralization assay were performed. The fact that antibodies of the present invention show neutraliztion over such a broad range of assays indicates that they are very strongly neutralizing.

The first assay used was a plaque assay which measures the inhibition of HIV infection of MT-2 cells to detect the neutralizing activity of the mAbs of the present invention in the presence or absence of human complement (C. V. Hanson et al., *J. Clin. Microbiol.*, 28:2030-4 (1990)). Thus, mAbs were serially diluted in 50% assay medium and 50% of a normal human plasma pool. The plasma pool served as the source of human complement; for studies in the presence of complement, mAb and virus were incubated for 18 hr at 37° C. For tests in the absence of complement, the plasma pool was heat-inactivated and the mAb and virus were incubated under these conditions for 1 hr at 37° C. The dilution at which 50% of the input virus was neutralized on the basis of plaque counts was calculated by interpolation using third order regression analysis of the mean plaque count at each dilution.

The second assay was the CEM-SS virus-induced syncytium-forming assay described by Nara, P. et al., in "Techniques in HIV Research," Aldovini et al., Eds., Stockton Press, New York, pp. 77+ (1990), which is a quantitative neutralization assay. Ninety-six well tissue culture plates were coated with poly-L-lysine, washed, and $5 \times 10^4$ exponentially growing CEM-SS cells (gift of P. Nara, NCI) were added to each well. Serial two-fold dilutions of 50 μl of mAb in RPMI 1640/10% heat inactivated FCS were incubated with 50 μl of viral supernatants ($1-2 \times 10^3$ syncytia forming units per ml) for one hour at room temperature. The cells were exposed to the virus-mAb mixture for one hour at 37° C. The virus-mAb mixture was then removed, and 100 μl of RPMI/10% FCS was then added. On day 3, 100 μl of medium were added. The syncytia were counted on day 5 or 6. The percent neutralization represents the ratio of the number of syncytia in each well to the number of syncytia in wells exposed to virus in the absence of antibody. All assays were run in duplicate. Note that at no time is human plasma used in this assay and that the antibody does not remain in the culture medium. The dilution at which 50% and 90% of the input virus was neutralized was calculated by using the IBM-PC program developed by Chou and Chou ("Dose-effect analysis with microcomputers," Biosoft, Cambridge (1989)).

The third assay quantitates neutralization of cellfree virus infection as well as the inhibition of cell-to-cell virus spread by measuring the cell survival after exposing cultures to antibody and virus for 7–8 days (Robertson, G. A. et al., *J. Virol. Meth.* 20:195 (1988)). In this manner, the monoclonal antibodies were tested for neutralization of lymphotrophic and lymphocytolytic isolates tested on MT-4 cells. Two-fold serial dilutions of the human monoclonal antibodies were made and 100 μl volumes were used in each test well. All virus stocks were made from available chronically infected H9 cells (IIIB, MN, RF) or from newly established chronically infected FDA/H9 cells (isolates SF-2, Al-1, WMJ-2, DU 6587-5, DU 7887-7). Virus stocks were prepared from clarified culture medium 72 hours after resuspension of the respective chronically infected cell line in fresh medium at a cell density of $2 \times 10^5$ cells/ml. For each virus stock of each isolate, an MT-4 cell infectivity endpoint was defined as the last dilution of the virus stock that killed essentially all MT-4 cells in a seven day assay. For consistency in neutralization tests, a dilution representing approximately 10-fold more than the minimum amount of the virus stock necessary to achieve complete kill was chosen. HIV-1 isolates used include: IIIB and RF (Popovic, M. et al., *Science* 224:497–500 (1984)), MN (Gallo, R. C. et al., *Science* 224:500–503 (1984)), AL-1 (Benn, S. et al., *Science* 230:94–951 (1985)), SF-2 (Levy, J. A. et al., *Science* 225:840–842 (1984)), WMJ-2 (Hahn, B. H. et al., *Science* 232:1548–1553), DU 6587-5 and DU 7887-7 (Scott, C. F., Jr. et al., *Proc. Natl. Acad. Sci. USA* 87:8597–8601). 100 μl of virus stock were added to each test well and the virus-antibody mixtures were inclubated at 37° C. for 1 hour after which $1 \times 10^4$ MT-4 cells in 50 μL of culture medium were added to each well. The cultures were incubated for 7 days when the antibody neutralization endpoint was determined (Robertston, G. A., *J. Virol. Meth.* 195–199 (1988)). The neutralization endpoints were determined as the last dilution of the antibody preparation that prevented MT-4 cell killing. Uninfected MT-4 cells were cultured with each test and a virus stock retitration was performed with each analysis.

A fourth assay measured inhibition of viral p24 production after exposure of monocyte/macrophage cultures to mAb and virus. The monocytotropic HIV isolate, SF-162, was used in this assay.

EXAMPLE V

Results of Antibody Analysis

Human mAbs 257-D and 268-D were produced by the method described in Example II and recently published in Gorny et al. (1991), supra. Using the method of Example III, 11 new heterohybridoma lines producing human mAbs against the V3 loop of gp120 from the MN strain of HIV-1 were established. These are all listed in Table 3. One human mAb, 694-D, was selected with $rgp120_{HTLV-IIIB}$, as described in Example III. The number of transformed lymphocytes used for fusion with SHMD33 usually ranged between 1.2 and $10 \times 10^6$ cells. However, in three cases, the number of antibody-producing transformed cells was insufficient and each of the three hybridoma lines (391/95-D, 447-D and 694-D) were generated by fusing a pool of cells obtained from two separate individuals. Thus, 12 cell lines were produced from 15 different HIV seropositive individuals. The hybridoma lines were cloned 3–5 times starting with density of 100 and/or 10 cells per well with at least two clonings at 1 cell per well. All but one line were found to produce subclass IgG1 antibodies. Line 447-D secreted an IgG3 antibody. Nine hybridoma lines produced mAb with λ and five lines with κ light chains (Table 3). The IgG concentration in the spent culture medium of the cell lines ranged from 10 to 50 μg/ml, except for lines 418-D and 477-D which produced less than 1 μg/ml of IgG. The specificity of the mAbs was tested first by ELISA. Thus far, all the mAbs have shown reactivity to the 23-mer peptide of $HIV_{MN}$ and, except for 412-D and 418-D, bind to the 20-mer peptide of $HIV_{SF2}$ coated on microtiter plates at concentrations ranging from 10 to 30 ng/ml. Two of the 14 mAbs, 447-D and 694-D reacted with the 22-mer peptide of HXB2 which was coated onto the plate at 200 and 100 ng/ml, respectively. Only one mAb, 694-D, reacted with $gp120_{HTLV-IIIB}$ on the commercial immunoblot (data not shown).

Figure 2:
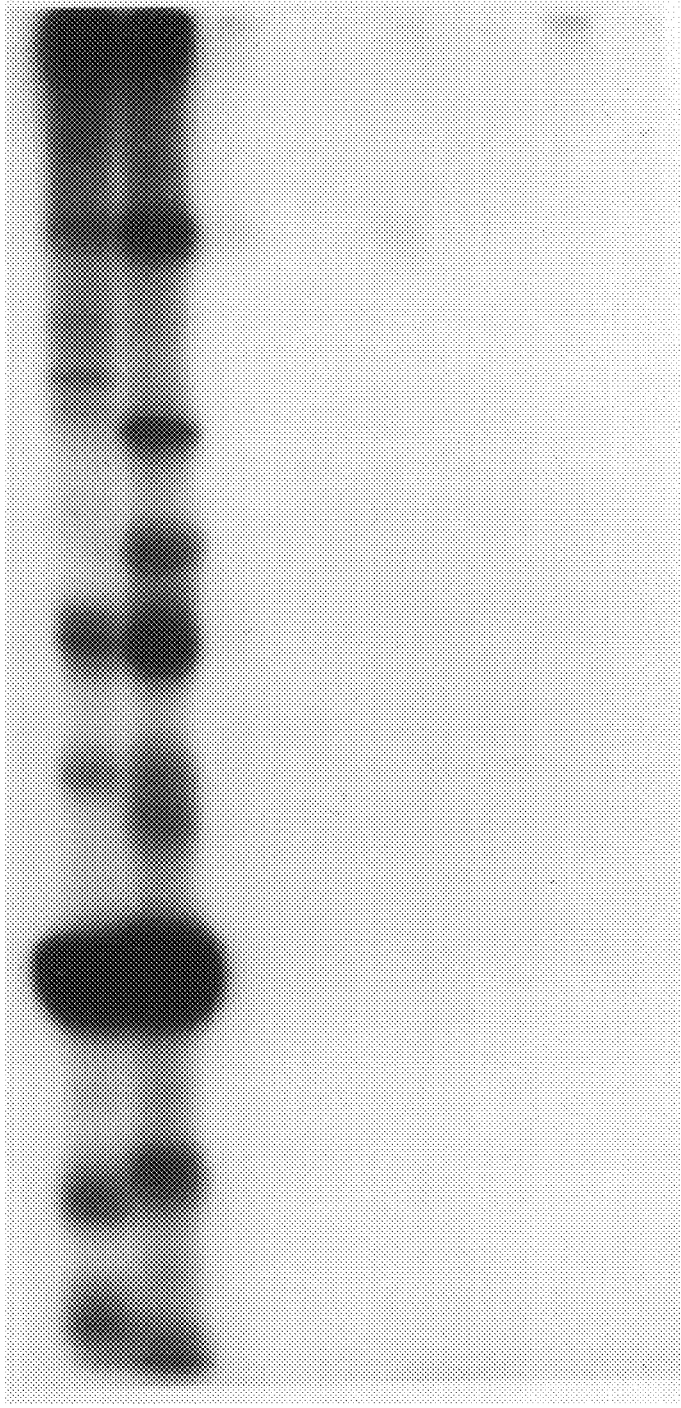
FIG. 2 is a gel pattern from a radioimmunoprecipitation assay of human mAbs with HIV lysates. Lanes 1 and 2 show the reactivity of a serum specimen from an HIV-infected individual. Lanes 3 and 4: reactivity of supernatant 257-D. Lanes 5 and 6: reactivity of supernatant 268-D. Lanes 7 and 8: reactivity of supernatant 280-2 (which is unreactive with HIV antigens). Lanes 1, 3, 5, and 7 represent the reactivity of specimens to $HIV_{MN}$ lysate. Lanes 2, 4, 6 and 8 represent reactivity of specimens to HTLV-IIIB lysate.
Figure 3:
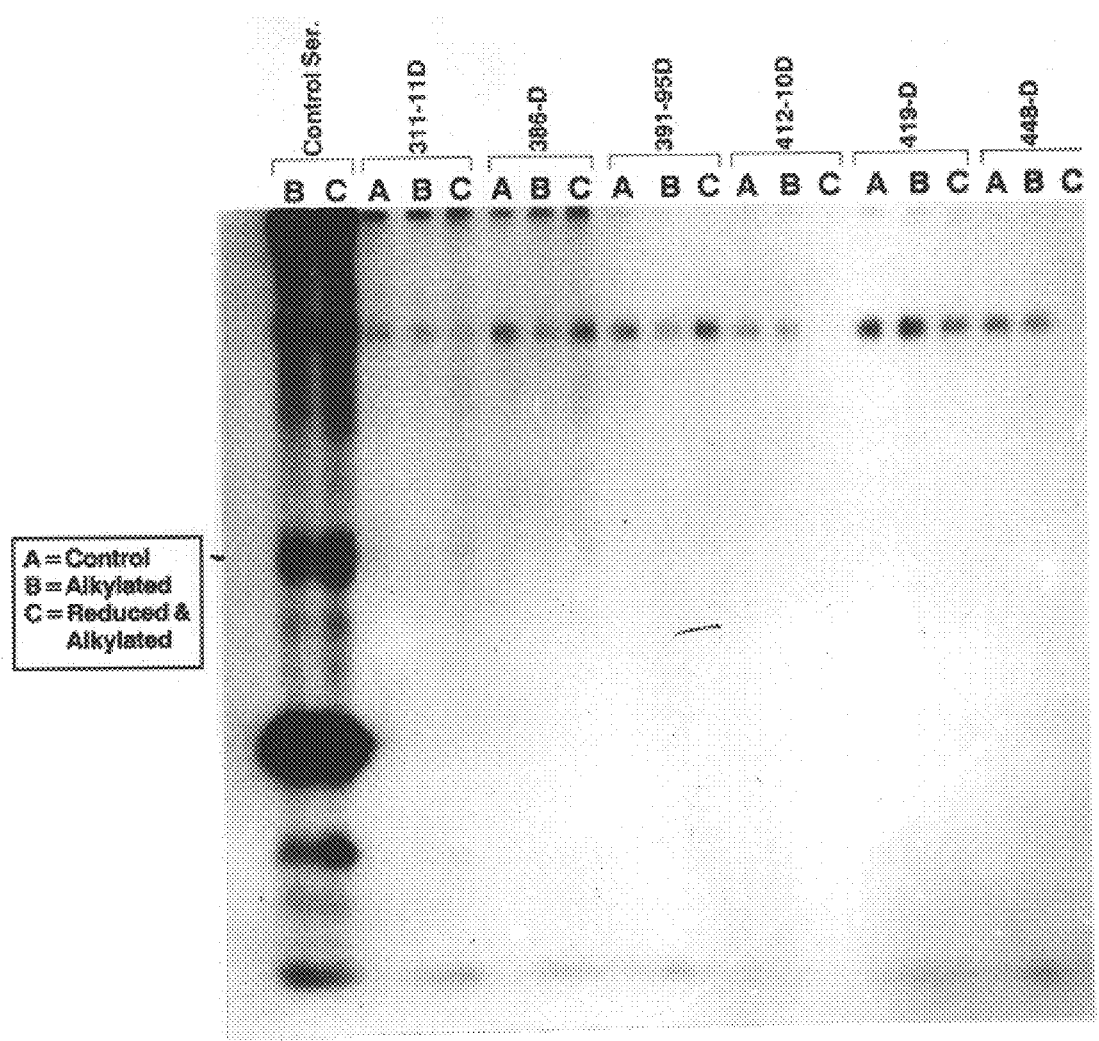
FIG. 3 is a gel pattern from a radioimmunoprecipitation assay of human mAbs with the $HIV_{MN}$ lysate. Reactivity of each sample is demonstrated with the non-reduced MN lysate (A lanes), alkylated (B lanes) and reduced and alkylated (C lanes). The first two lanes (B and C) represent the reactivity of a serum specimen from an HIV-positive individual. The following six samples are: human mAbs directed against the V3 loop of MN (311-11D, 386-D, 391/95-D, 412-10D and 419-D) and against the CD4-binding domain of gp120 (448-D). The two mAbs, 448-D and 412-D, do not bind to the linear antigen (C); 448-D recognizes the conformational antigen only and 412-D needs a higher concentration for binding to reduced gp120.

Further characterization of these mAbs was determined by RIP. As shown in FIG. 2, mAbs 257-D and 268-D react with the env-encoded protein gp120 of HIV$_{MN}$ but not with the gp120 derived from HTLV-IIIB, revealing the limited reactivity of these mAbs. As shown in FIG. 3, all of the mAbs tested therein reacted with gp120 of untreated HIV$_{MN}$ lysate. When HIV$_{MN}$ lysate was reduced (dithiothreitol treated and alkylated) all mAbs except one bound to gp120. Antibody 412-D did not react with reduced viral lysate at a concentration of 9 μg/ml, but when it was concentrated by ammonium sulfate precipitation to 60 μg/ml trace, reaction with gp120 was observed. These results indicate that all the mAbs shown in FIG. 3 recognized linear epitopes. The weak binding of 412-D to the reduced form of gp120 could be attributed to low mAb affinity and/or partial dependence on conformational contributions to the epitope (Table 3). In an ELISA format, 412-D bound well to the peptide coat at the saturated concentration (1 μg/ml) because the antibody binding in such conditions is independent of affinity (Nimmo, R., *J. Immunol. Methods* 72:177 (1984)).

Fine mapping of the epitopes of these mAbs was determined by the Epitope Mapping Kit. When 18 overlapping hexapeptides were synthesized in situ on plastic pins that spanned the 23-mer peptide, the epitopes for seven mAbs were found. The epitopes contained four, five,six or seven amino acid sequences. For the other mAbs, 17 overlapping heptapeptides were synthesized, and epitopes for five more mAbs were found. These epitopes contained seven amino acid sequences. Two mAbs, 391/95-D and 412-D, reacted only with heptamers, in each case binding to seven overlapping heptapeptides. Due to this high number of reactive peptides, a core epitope could not be determined. Both mAbs also reacted with a 15-mer peptide from V3$_{MN}$. The isotype, RIP reactivity and core epitope of the various human mAbs of the present invention are shown in Table 3.

TABLE 3

Human mAbs Against the V3$_{MN}$ loop of gp120

| Human mAb | Isotype | Reactivity by RIP | Epitope | Residue numbers from SEQ ID NO:1 |
|---|---|---|---|---|
| 257-D | IgG1λ | gp120 | KRIHI | 10–14 |
| 268-D | IgG1λ | gp120 | HIGPGR | 13–18 |
| 311-11D | IgG1λ | gp120 | KRIHIGP | 10–16 |
| 386-D | IgG1λ | gp120 | HIGPGR | 13–18 |
| 391/95-D | IgG1κ | gp120 | * | 9–23 |
| 412-D | IgG1κ | gp120 | * | 9–23 |
| 418-D | IgG1κ | gp120 | HIGPGRA | 13–19 |
| 419-D | IgG1λ | gp120 | IHIGPGR | 12–18 |
| 447-D | IgG3λ | gp120 | GPGR | 15–18 |
| 453-D | IgG1λ | gp120 | IHIGPGR | 12–18 |
| 477-D | IgG1κ | gp120 | HIGP | 13–16 |
| 504-D | IgG1κ | gp120 | IHIGPGR | 12–18 |
| 537-D | IgG1λ | gp120 | IGPGR | 14–18 |
| 694-D | IgG1λ | gp120 | GRAF | 17–20 |

*Reactive with 15-mer from V3$_{MN}$ (RKRIHIGPGRAFYTT)

Figure 4A:
FIG. 4A and B are graphs showing the results of a scan of serum and mAb reactivities by ELISA with overlapping hexapeptides homologous with the 23-mer of the $HIV_{MN}$ V3 loop. The reactivity of each hexapeptide with seronegative (□) or seropositive (□) sera (FIG. 4A) or with supernatants from heterohybridomas 257-D (□) or 268-D (■) (FIG. 4B) is shown on the ordinate and each hexapeptide is designated by the single letter code of its N-terminal residue and the subsequent five amino acids. Thus, the sequence appearing on the abscissa is the sequence of the 23-mer (residues 6–28 of SEQ ID NO:1).
Figure 4B:
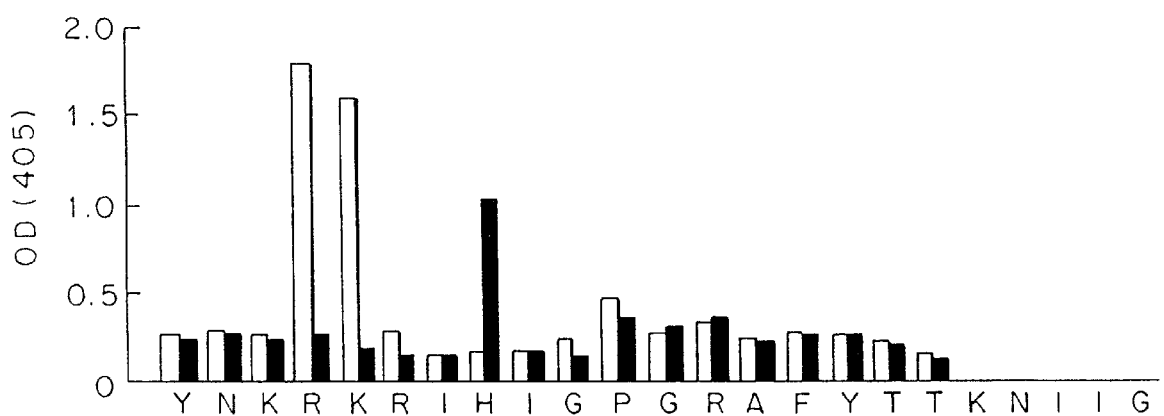

To illustrate how the reactive epitopes were determined, an example of the data obtained from the mapping experimented for two of the mAbs, 257-D and 268-D, is shown in Table 4 and FIGS. 4A and 4B. These data show that a pool of seronegative sera was not reactive. Table 4 shows the overlapping antigenic regions recognized by the two mAbs.

TABLE 4

REACTIVITY OF HUMAN SERA AND HUMAN MONOCLONAL ANTIBODIES WITH HEXAPEPTIDES OF THE MN gp120 V3 LOOP

| | | ELISA REACTIVITY (Absorbance units) | | | |
|---|---|---|---|---|---|
| PIN# | Hexapeptide* | HIV+ Serum | HIV– Serum | 257-D | 268-D |
| 3 | YNKRKR | .338 | .195 | .256 | .243 |
| 4 | NKRKRI | .339 | .200 | .288 | .283 |
| 5 | KRKRIH | .251 | .184 | .259 | .239 |
| 6 | RKRIHI | .308 | .183 | 1.781 | .252 |
| 7 | KRIHIG | .286 | .170 | 1.592 | .179 |
| 8 | RIHIGP | .302 | .177 | .276 | .135 |
| 9 | IHIGPG | .267 | .197 | .130 | .132 |
| 10 | HIGPGR | .269 | .185 | .156 | 1.011 |
| 11 | IGPGRA | .361 | .191 | .163 | .164 |
| 12 | GPGRAF | .243 | .103 | .208 | .132 |
| 13 | PGRAFY | .586 | .237 | .456 | .346 |
| 14 | GRAFYT | .582 | .239 | .272 | .288 |
| 15 | RAFYTT | .658 | .239 | .333 | .350 |
| 16 | AFYTTK | .257 | .197 | .233 | .222 |
| 17 | FYTTKN | .384 | .233 | .273 | .274 |
| 18 | YTTKNI | .362 | .171 | .259 | .259 |
| 19 | TTKNII | .284 | .191 | .219 | .212 |
| 20 | TKNIIG | .305 | .198 | .164 | .141 |

*Overlapping hexapeptides from 6–11, 7–12 . . . through 23–28 of SEQ ID NO:1

A seropositive serum sample (serum from an HIV-seropositive individual at a dilution of 1:1000) reacted above background levels with all pins, giving peak reactions with three pins spanning the region P G R A F Y T T (residues 16–23 of SEQ ID NO:1) at the tip and right side of the V3 loop. MAb 257-2D, at a dilution of 1:10 (3.7 μg/ml), bound strongly to two adjacent hexapeptides representing amino acid 309–315 (R KR-I-H-I-G) to the left of the top of the loop (residues 9–15 of SEQ ID NO:1) . MAb 268-11D (5.4 μg/ml) bound to one hexapeptide covering the amino acid sequence H-I-G-P-G-R (residues 13–18 of SEQ ID NO:1).

These results indicate that the smallest reactive peptide (core of the epitope) that 257-D recognizes is KRIHI (residues 10–14 of SEQ ID NO:1), located to the left of the conserved tip of the V3 loop. The flanking N- and C-terminal arginine and glycine residues may also contribute to the binding of this mAb. The mAb 268-D binds to a single hexapeptide consisting of H I G P G R (residues 13–18 of SEQ ID NO:1) which spans the tip of the loop and the two adjacent N-terminal amino acids. The epitopes for the remaining mAbs were determined analogously.

A total of nine different epitopes were delineated, which were contained within the 11 amino acid sequences of KRIHIGPGRAF (residues 10–20 of SEQ ID NO:1) (FIG. 5). The epitopes included part of or the whole tip GPGR (residues 15–18 of SEQ ID NO:1) of the loop which is the most conserved sequence of the V3. Only mAb 257-D, which reacts to KRIHI (residues 8–14 of SEQ ID NO:1), recognized an epitope found outside of the GPGR (residues 15–18 of SEQ ID NO:1) sequence. The two epitopes HIGPGR and IHIGPGR (residues 13–18 and 12–18 of SEQ ID NO:1, respectively) were recognized by the five mAbs, 268-D, 386-D and 419-D, 453-D, 504-D, respectively. The two mabs, 447-D and 694-D, which recognized the epitopes GPGR (residues 15–18 of SEQ ID NO:1) and GRAF (residues 17–20 of SEQ ID NO:1), respectively, bound to 8 different types of the V3 loop peptide that have the same or similar sequence. Table 5 shows the ELISA reactivity of 447-D, 694-D and 537-D with ten V3 peptides performed as described by Gorney et al., 1989, supra.

TABLE 5

IMMUNOCHEMICAL CHARACTERISTICS OF ANTI-V3 HuMoAbs

| Human Monoclonal Antibody: | | 447-D | 694-D | 537-D |
|---|---|---|---|---|
| ELISA Reactivity vs. | | | | |
| V3-MN | (GPGRAF)[a] | +(0.01)[g] | +(0.01) | +(0.6) |
| V3-SF-2 | (GPGRAF)[a] | +(0.01) | +(0.01) | +(1.0) |
| V3-HXB2 | (GPGRAF)[a] | +(0.2) | +(0.1) | — |
| V3-RF | (GPGRVI)[b] | +(0.4) | +(1.0) | — |
| V3-WM52 | (GPGRAF)[a] | +(0.2) | +(0.6) | +(2.0) |
| V3-NY5 | (GPGRTL)[c] | +(0.1) | +(1.00) | +(0.8) |
| V3-SC | (GPGRAF)[a] | +(0.01) | +(0.02) | +(1.0) |
| V3-CDC4 | (GPGRVW)[d] | +(0.1) | +(1.00) | +(1.0) |
| V3-SF33 | (GPGKVL)[e] | — | — | — |
| V3-ELI | (GLGQSL)[f] | — | — | — |

[a]Residues 15–20 of SEQ ID NO:1
[b]Residues 12–17 of SEQ ID NO:12
[c]SEQ ID NO:13
[d]SEQ ID NO:14
[e]SEQ ID NO:15
[f]SEQ ID NO:16
[g]ELISA reactivity is noted for the minimum antigen concentration giving positive results (in μg/ml of V3 peptide used to coat ELISA plates). Negative results reflect lack of reactivity atconcentrations from 0.01–2.0 μg/ml. Human mAbs were used at concentrations of 10 μg/ml.

TABLE 6

AFFINITY OF ANTI-V3 MABS FOR V3 PEPTIDES OF DIVERGENT STRAINS

| | | Affinity ($K_d$ $10^{-6}$M) | | | |
|---|---|---|---|---|---|
| Hu mAbs | Epitope[a] | MN | SF-2 | | HXB2 |
| 447-D | GPGR | 0.56 | 0.9 | (GPGR)[b] | 24.0 (GPGR) |
| 694-D | GRAF | N.T. | 1.8 | (GRAF) | 12.0 (GRAF) |
| 257-D | KRIHI | 0.23 | 0.22 | (K<u>S</u>I<u>Y</u>I) | — |
| 537-D | IGPGR | 1.3 | 8.5 | (IGPGR) | >100 |
| 268-D | HIGPGR | 0.59 | 2.3 | (<u>Y</u>IGPGR) | — |
| 386-D | HIGPGR | 0.18 | 0.85 | (<u>Y</u>IGPGR) | — |
| 419-D | IHIGPGR | 3.8 | 0.23 | (<u>T</u><u>Y</u>IGPGR) | — |
| 453-D | IHIGPGR | 1.6 | 3.1 | (<u>T</u><u>Y</u>IGPGR) | — |
| 504-D | IHIGPGR | 0.35 | 0.83 | (<u>T</u><u>Y</u>IGPGR) | — |
| 418-D | HIGPGRA | 0.24 | — | (<u>Y</u>IGPGRA) | — |
| 311-11D | KRIHIGP | 7.4 | 6.0 | (K<u>S</u><u>I</u><u>Y</u>IGP) | — |
| 391/85-D | * | 0.91 | 4.4 | | — |
| 412-D | * | 9.1 | — | | — |

*Reactive with 15-mer from tip of V3 loop
—Not reactive in ELISA
[a]Subsets of residues 10–20 of SEQ ID NO:1
[b]Sequence of V3 SF-2 related to MN epitope. Underlined letters indicate amino acid which differs in comparison to MN sequence. Epitopes are subsets of residues 5–15 of SEQ ID NO:17.

The affinity of these mAbs expressed as the dissociation constant ($K_d$) was determined by using the method of Friguet et al. (Friguet, B. et al., *J. Immunol. Methods* 77:305 (1985)), (Tables 6 and 7). Peptides (20-mer and 22-mer) from American Bio-Technologies were used for the measurements. The $K_d$ values for the 20-mer of HIV$_{MN}$ ranged between $0.18 \times 10^{-6}$M and $9.1 \times 10^{-6}$M. The $K_d$ values for the 20-mer of HIV$_{SF2}$ were generally higher (affinity lower) than those for HIV$_{MN}$ with one exception. Antibody 419-D had a higher affinity (one order of magnitude) for the SF-2 than for the MN peptide with a $K_d$ of $0.23 \times 10^{-6}$ and $3.8 \times 10^{-6}$M, respectively. The binding of mAbs to the MN and SF-2 peptides indicate cross-reactivity which partly depends on the sequence of the core epitopes. A comparison of epitope sequence and affinity suggests that other factors, such as conformation, may play an additional role in binding (Table 6). Three mAbs, 447-D, 537-D and 694-D, recognized epitopes that are the same in the MN and SF-2 peptides. However, the affinity was not the same and for 537-D the $K_d$ value differed 7-fold for the two V3 peptides. Six mAbs reacted with epitopes which differed in one amino acid in sequence. Two mAbs, 257-D and 311-11D, bound to epitopes different in sequence for two amino acids, but the affinity for both V3 peptides was the same or very similar. Two mAbs, 447-D and 694-D, reacted with the 22-mer HXB2. Their $K_d$ values were 1 to 2 orders of magnitude higher (affinity weaker) than for the MN and SF-2 peptides, even though the mAbs recognized the epitopes GPGR and GRAF (residues 15–18 and 17–20, respectively, of SEQ ID NO:1) which are present in the same sequence in all three peptides. The affinity of 447-D changed for the HXB2 but not for the MN peptide during the course of cloning. After the second cloning at 10 and 1 cells per well, the $K_d$ for the HXB2 peptide was $64 \times 10^{-6}$M. However, after the fourth cloning at 10 cells/well and three consecutive clonings at 1 cell/well, the $K_d$ for the HXB2 peptide decreased to $16 \times 10^{-6}$M.

TABLE 7

COMPARISON OF THE AFFINITIES OF ANTI-V3 MABS FOR A V3 PEPTIDE VS. RECOMBINANT SF-2

| | $K_d$ (M) | | |
|---|---|---|---|
| mAb | SF-2 Peptide | SF-2 Recombinant | Difference |
| 257-D | $0.63 \times 10^{-6}$ | $4.16 \times 10^{-8}$ | 15-fold |
| 386-D | $2.59 \times 10^{-6}$ | $4.78 \times 10^{-8}$ | 54-fold |
| 391/95-D | $3.59 \times 10^{-6}$ | $56.9 \times 10^{-8}$ | 6-fold |
| 419-D | $0.15 \times 10^{-6}$ | $3.94 \times 10^{-8}$ | 4-fold |

The affinity of all the mAbs for the MN and SF2 peptides was not found to correlate with the number of amino acids in each epitope (from 4 to 7 a.a.). These $K_d$ values reflect the reaction between mAbs and 20- or 22-mer peptides. The $K_d$ of mAbs for recombinant protein may well be quite different due to tertiary and quaternary structure of the whole molecule which may contribute to the epitopes recognized by mAbs. The $K_d$ of the mAbs to recombinant gp120 protein of HIV$_{SF2}$ (produced in CHO cells) was compared to that of the 20-mer SF-2 peptide that spans the V3 loop. The $K_d$ values for the recombinant protein were 4- to 54-fold lower (affinity higher) than for the 20-mer peptide (Table 7).

The human mAbs were tested for their neutralization ability by means of the several neutralization assays described in Example IV. Using the first assay (Hanson, 1990, supra), when supernatant fluids from 257-D and 268-D were incubated with HIV$_{MN}$ for 1 hr (no complement) prior to addition to permissive MT-2 cells, 50% neutralization was achieved at dilutions of 1:4,700 and 1:2,000, corresponding to mAb concentrations of 3.0 and 23.0 ng/ml, respectively (Table 8). No neutralization of HTLV-IIIB was observed.

When the mAbs from 257-D and 268-D were tested in a more sensitive assay, wherein antibodies were incubated with virus for 18 hours in the presence of human complement, neutralization was achieved at dilutions of 1:44,000 and 1:41,000, corresponding to mAb concentrations of 0.3 and 1.1 ng/ml, respectively. Again, no neutralization of HTLV-IIIB occurred under these conditions.

Figure 6A:
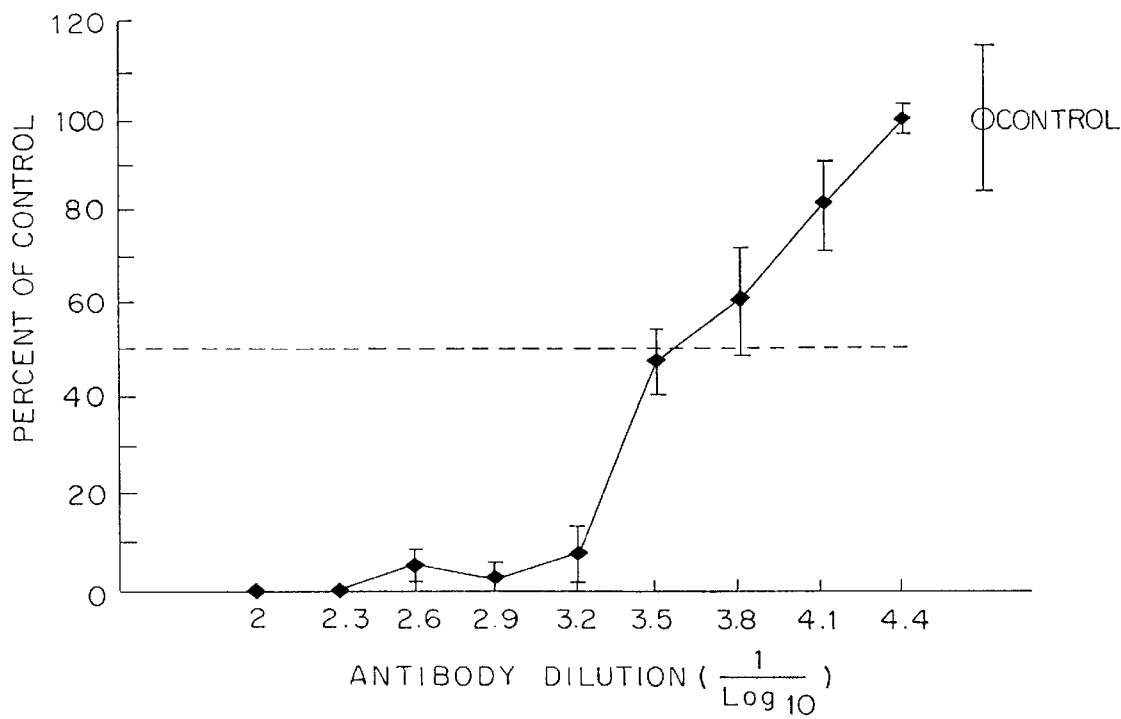
FIGS. 6A and B are graphs showing HIV neutralization by serial dilutions of mAb 257-D (starting concentration: 14.0 μg/ml).
Figure 6B:
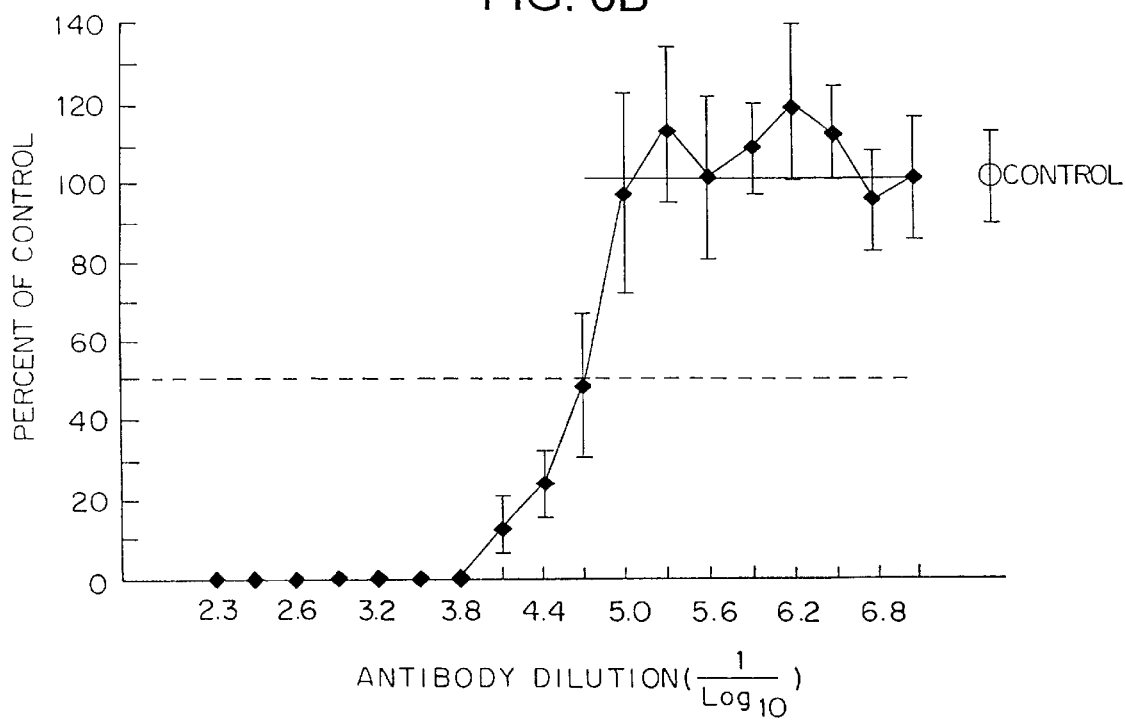
FIG. 6B: Neutralization of $HIV_{MN}$ incubated with 257-D in the presence of complement for 18 hrs. The data are normalized as the percentage of the mean plaque count in 12 or 24 replicate control wells (○) for experiments shown in FIG. 6A and 6B, respectively. The number of control plaques in the experiment shown in FIG. 6A was 9.6±1.4 (Mean±SEM) and, in FIG. 6B, 9.1±1.1. Error bars represent the standard error (SEM).

Representative dose-response curves for the activity of mAb 257-D against HIV$_{MN}$ in the absence and presence of complement, is shown in FIGS. 6A and 6B. Human mAb 50–69, specific for the HIV transmembrane protein, gp41, and mAb 71–31, specific for the core protein, p24, previously described by Gorny, M. K. et al., *Proc. Natl. Acad. Sci. USA* 86:1624–1628 (1989)), were tested in parallel and displayed essentially no neutralizing activity for either strain of HIV.

TABLE 8

NEUTRALIZING ACTIVITY OF HUMAN MONOCLONAL ANTIBODIES AGAINST HIV

| | | Neutralizing Antibody Titers (ng/ml) | | | |
|---|---|---|---|---|---|
| | | 1 hr, no C[1] | | 18 hr + C[1] | |
| mAb | Specificity | MN | IIIB | MN | IIIB |
| 257-D | gp120 | 1:4700 (3) | neg | 1:44000 (0.3) | neg |
| 268-D | gp120 | 1:2000 (23) | neg | 1:41000 (1.1) | neg |
| 50–69 | gp4l | 1:3 | neg | 1:3 | neg |
| 71–31 | p24 | neg | neg | neg | neg |

Figure 7:
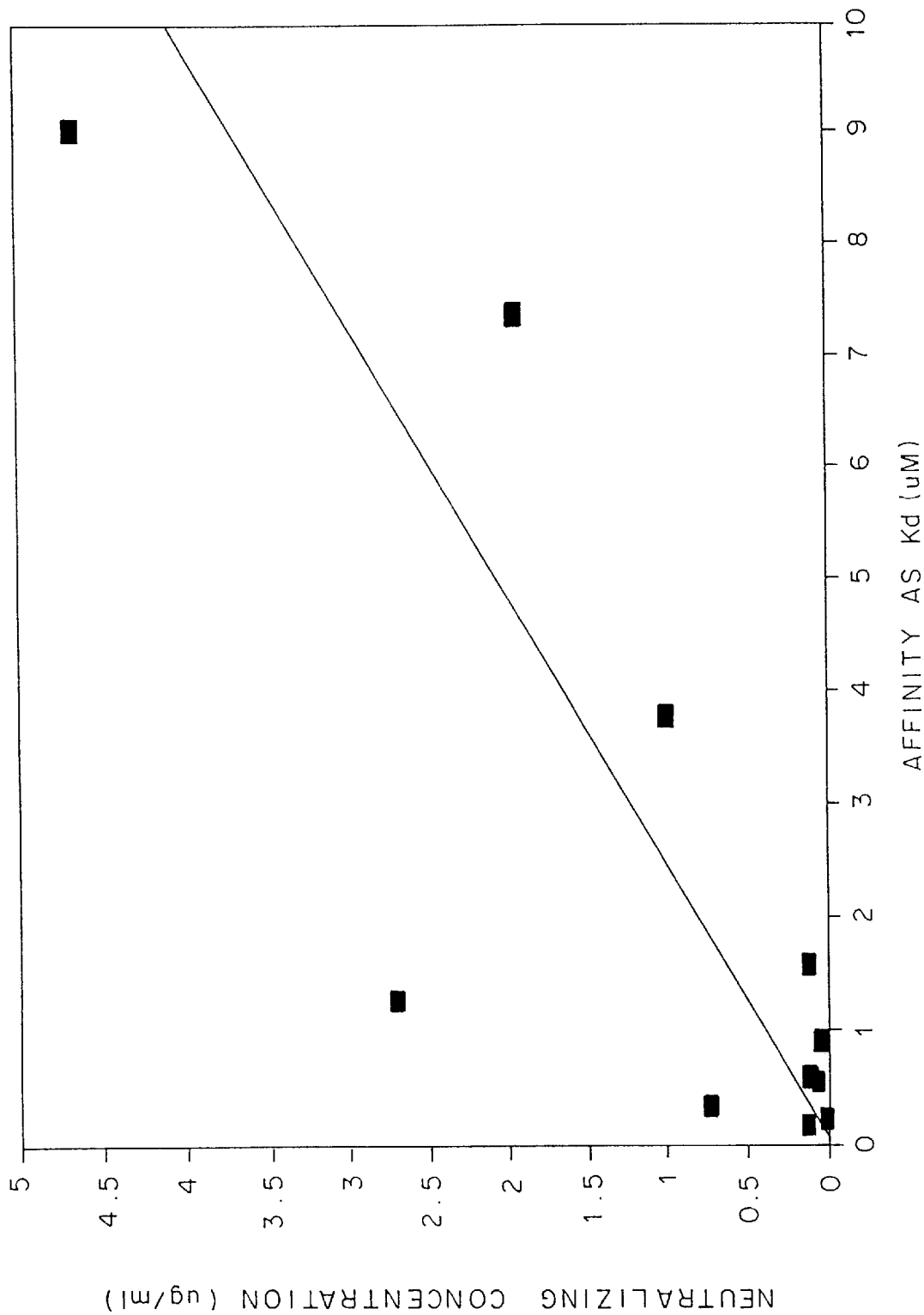
FIG. 7 shows the correlation (R=0.82) between the dissociation constants ($K_d$) and the neutralization capacity for the ani-V3 MN human mAbs. The affinity for the 23-mer peptide of V3 MN was determined by ELISA according to the method of Friguet et al. (Friguet et al., J. Immunol. Methods 77:305–319 (1985)). The neutralization of $HIV_{MN}$ was performed using the syncytium-forming assay described by Nara (Nara, P. et al., in "Techniques in HIV Research," Aldovini et al., Eds., Stockton Press, New York, pp. 77+ (1990)).

Using the second assay (Nara, 1990, supra), all the mAbs tested neutralized the $HIV_{MN}$ at concentrations of 12 to 4697 ng/ml (50% neutralization) (FIG. 7, Table 9). Six mAbs neutralized 90% of $HIV_{MN}$ at concentrations below 2000 ng/ml while the others required concentration above 10,000 ng/ml of IgG. Only two of the 14 mabs, 447-D and 694-D, neutralized HTLB-IIIB at a concentration similar in range to $HIV_{MN}$.

TABLE 9

THE AFFINITY AND NEUTRALIZING ACTIVITY OF HUMAN ANTI-V3$_{MN}$ MAB

| | | neutralization | | | |
|---|---|---|---|---|---|
| | $K_d$ | MN | | IIIB | |
| HumAb | ×10$^{-6}$M | 50% | 90% | 50% | 90% |
| 386-D | 0.18 | 0.11[a] | 1.58[a] | — | — |
| 257-D | 0.23 | 0.01 | 0.88 | — | — |
| 418-D | 0.24 | 0.01 | 1.78 | — | — |
| 504-D | 0.35 | 0.72 | >10[b] | — | — |
| 447-52-D | 0.56 | 0.05 | 0.92 | 1.8 | >10 |
| 268-D | 0.59 | 0.10 | 1.00 | — | — |
| 391/95-D | 0.91 | 0.04 | 0.87 | — | — |
| 537-D | 1.3 | 2.69 | >10 | — | — |
| 453-D | 1.6 | 0.10 | 3.08 | — | — |
| 419-D | 3.8 | 0.99 | >10 | — | — |
| 311-11D | 7.4 | 1.97 | >10 | — | — |
| 412-D | 9.1 | 4.69 | >10 | — | — |
| 694/98-D | NT | NT | NT | 0.04 | 1.4 |

[a]IgG concentration (μg/ml)
[b]Did not achieve 90% neutralization at the highest concentration tested, 10 μg/ml
NT - Not Tested Several mAbs neutralized $HIV_{MN}$ at relatively high concentration of IgG and these mAbs had lower affinity to the MN 20-mer peptide. A significant correlation (R=0.82) was demonstrated between the 50% neutralizing concentration and the dissociation constants of mAbs (FIG. 7). Thus, the lower affinity of the mAb for V3, the more mAb is needed to neutralize the virus.

Using the third assay (Robertson, 1988, supra), the action of 447-D was tested on eight strains of HIV-1 (Table 10). All isolates tested bore the GPGR (residues 15–18 of SEQ ID NO:1) motif in the V3 loop, but represent divergent branches of the HIV-1 family (Myers et al., supra; LaRose et al., supra). Neutralization endpoints for lymphotropic isolates were attained at geometric mean concentrations ranging from 0.04 to 1.35 μg/ml. By comparison, the neutralization endpoint of 447-D for IIIB is equivalent to that of human-mouse chimeric antibody Cβ1, one of the most potent anti-IIIB type-specific antibodies known.

The fourth assay, measuring inhibition of viral p24 production after exposure of monocyte/macrophage cultures to mAb and virus, was used to test the effects of 447-D on the monocytotropic HIV isolate, SF-162. Endpoint neutralization in this assay was obtained with 1.98 μg/ml antibody. The results are shown on the last line of Table 10.

TABLE 10

Neutralization of HIV Infectivity in vitro by 447-D*

| Virus Isolate | V3 Loop Sequence | SEQ ID NO: | Geometric Mean (range) of Neutralization Endpoint in μg/ml |
|---|---|---|---|
| IIIB | TRKSIRIQRGPGRAFVTIGKIG | 2 | 1.29 (0.39–1.56) |
| MN | YNKRKRIHIGPGRAFYTTKNII | 1[a] | 0.37 (0.04–0.78) |
| AL-1 | IYRKGRIHIGPGRAFHTTRQII | 18 | 0.15 (0.09–0.19) |
| SF-2 | NNTRKSIYIGPGRAFHTTGRII | 17 | 0.04 (0.04) |
| DU 6587-5 | SNVRNRIHIGPGRAFHTTKRIT | 19 | 0.62 (0.39–0.78) |
| WMJ-2 | NNVRRSLSIGPGRAFRTREIIG | 20 | 1.35 (0.78–1.56) |
| DU 7887-7 | NNTSRGIRIGPGRAILATERII | 21 | 0.78 (0.78) |
| RF | NNTRKSITKGPGRVIYATGQII | 12 | 0.62 (0.39–0.78) |
| SF-162 | NNTRKSITIGPGRAFYATGDII | 22 | 1.98 (1.25–2.50) |

*For SF-162 virus, neutralization was measured in monocyte macrophage culture. For the other viral isolates, neutralization was based on a MT-4 cell killing assay.
[a]Residues 6–27

It is important to note the differences of the 447-D antibody and the 694-D antibody from the antibodies described by Ohno et al. (supra), Åkerblom et al (supra), and Scott et al. (supra). Ohno et al. have discovered a broadly reactive mAb against several HIV-1 strains. However, this is a murine mAb which, for a variety of reasons noted above, has limited utility in human therapy. Potential limitations, noted by Scott et al., are lower activity of murine antibodies in antibody-dependent cellular cytotoxicity and the undesirable and potentially dangerous immunogenicity of the murine antibody for human recipients. The human mAb N701.9b disclosed by Scott et al. (supra) does not have these particular disadvantages. However, this mAb is type-specific, and therefore potentially useful only for treating infections with the MN strain of HIV1. The human mAbs of the present invention, such as 447-D and 694-D, encompass the full array of desirable features, namely lack of foreign (murine) antigens, broad reactivity against diverse HIV-1 strains, and potent virus neutralizing activity. Indeed, the reactivity is broader even than that of the murine antibodies of Ohno et al. (supra) and Åkerblom et al. (supra)

The third assay was also used to determine the neutralization activity of mAbs 447-D, 537-D and 694-D as compared to the anti-CD4-bd mAbs 448-D, 559-D and 588-D against lymphotrophic and lymphocytolytic isolates tested on MT-4 cells. The results are shown in Table 11.

TABLE 11

| HIV-1 | | SEQ ID | Neutralization endpoint (µg/ml) of in vitro MT-4 cell killing assay* | | | | | |
| | | | anti-V3 | | | anti-CD4-bd | | |
| Isolate | V3 Loop Sequence | NO: | 447-52-D | 537-D | 694/98-D | 448-D | 559-D | 558-D |
|---|---|---|---|---|---|---|---|---|
| IIIB | TRKSIRIQRGPGRAFVTIGKIG | 2 | 1.29 | >50 | 0.78 | 6.25 | 6.25 | 6.25 |
| MN | YNKRKRIHIGPGRAFYTTKNII | 1[a] | 0.37 | 6.25 | 3.13 | >25 | 1.56 | 6.25 |
| AL-1 | IYRKGRIHIGPGRAFHTTRQII | 18 | 0.15 | 3.13 | 0.04 | 0.09 | 0.39 | 0.78 |
| SF-2 | NNTRKSIYIGPGRAFHTTGRII | 17 | 0.04 | >5 | 0.04 | ≦0.04 | ≦0.09 | 0.39 |
| DU 6587-5 | SNVRNRIHIGPGRAFHTTKRIT | 19 | 0.62 | N.D.** | N.D. | N.D. | N.D. | N.D. |
| WMJ-2 | NNVRRSLSIGPGRAFRTREIIG | 20 | 1.35 | >50 | 6.25 | >12.5 | 50 | >50 |
| DU 7887-7 | NNTSRGIRIGPGRAILATERII | 21 | 0.78 | N.D. | >25 | >12.5 | >50 | >50 |
| RF | NNTRKSITKGPGRVIYATGQII | 12 | 0.62 | >50 | >25 | >12.5 | >50 | 6.25 |

*Data for 447-D represent geometric mean titres from 3–8 experiments; data for other human mAbs are derived from single experiments.
**N.D., not done.
[a]Residues 6–27

These studies demonstrate that an anti-V3 domain human mAb exhibits greater virus neutralizing potency and is more broadly reactive than comparable antibodies to the CD4-bd. The broad neutralizing activity of 447-D is due to its ability to bind to the GPXR (SEQ ID NO:11) determinant. This sequence is present in approximately 80% of V3 domain sequences that have been derived from HIV-1 isolates in North America and Europe (LaRosa, G. J. et al., *Science* 249:932–945 (1991)). This sequence is not as prevalent among African HIV-1 isolates (Myers, G. et al., *Theoretical Biology and Biophysics*, Los Alamos (1991)). Yet, within the limits of this geographical restriction, this antibody may be used as an immunoprophylactic and immunotherapeutic agent. Moreover, these results directly demonstrate that a broadly reactive anti-V3 antibody of significant virus neutralizing potency can be elicited in humans.

EXAMPLE VI

Further Identification of 447-D and 694-D Epitopes

To further identify the epitope with which 447-D and 694-D reacted, the mAbs were tested with a set of 18 over-lapping hexapeptides or heptapeptides, respectively, spanning the region of V3$_{MN}$ represented by the 23-mer used originally for screening in the process of producing the mAb, i.e., sequences corresponding to residues 306–328 of the gp120 MN envelope. Each hexapeptide or heptapeptide overlaps with its neighbor by 5 or 6 amino acids. The hexapeptides or heptapeptides were synthesized in situ on polyethylene pins using the method of Geyson et al. (supra) and were reacted with culture supernatants containing 29 µg mAb/ml. The results are shown in FIG. 8.

FIG. 8 shows that 447-D reacted with three hexapeptides: HIGPGR, IGPGRA and GPGRAF (residues 13–18, 14–19 and 15–20, respectively, of SEQ ID NO:1). These results suggest that the epitope recognized by 447-D is h-i-G-P-G-R-a-f (residues 13–20 of SEQ ID NO:1), wherein the upper case letters represent the core of the epitope and the lower case letters represent flanking amino acids which may also contribute to binding.

The results for 694-D are also shown in FIG. 8, as well as Table 12. These results establish that the epitope recognized by this antibody is GRAF (residues 17–20 of SEQ ID NO:1).

TABLE 12

Epitope Mapping of 694-D

| Pin | Heptapeptide* | ELISA Reactivity** |
|---|---|---|
| 10 | HIGPGRA | 0.140 |
| 11 | IGPGRAF | 1.374 |
| 12 | GPGRAFY | >2.000 |
| 13 | PGRAFYT | 1.401 |
| 14 | GRAFYTT | 1.234 |
| 15 | RAFYTTK | 0.089 |

*Subsets of residues 13–24 of SEQ ID NO:1
**Values represent the absorbance at 410 nm of the human mAb at a concentration of 10 µg/ml.

Figure 9A:
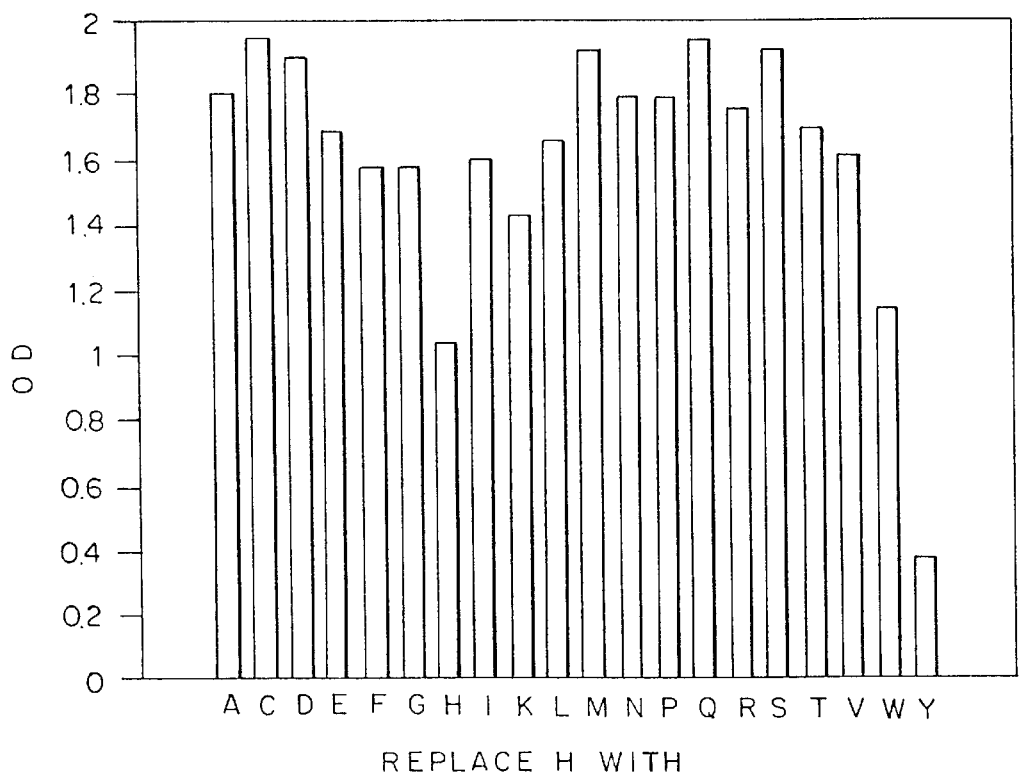
FIGS. 9A–9F represent is a series of graphs showing a "replacement set analysis." The replacement set of peptides is based on the parent peptide HIGPGR (corresponding to residues in the 313–328 tip of the V3 loop of gp120 (residues 13–18 of SEQ ID NO:1)). Each block of 20 ELISA results represents the unmodified and 19 amino acid substitutions at each position in the HIGPGR sequence. The substituting residue is designated below each bar.
Figure 9B:
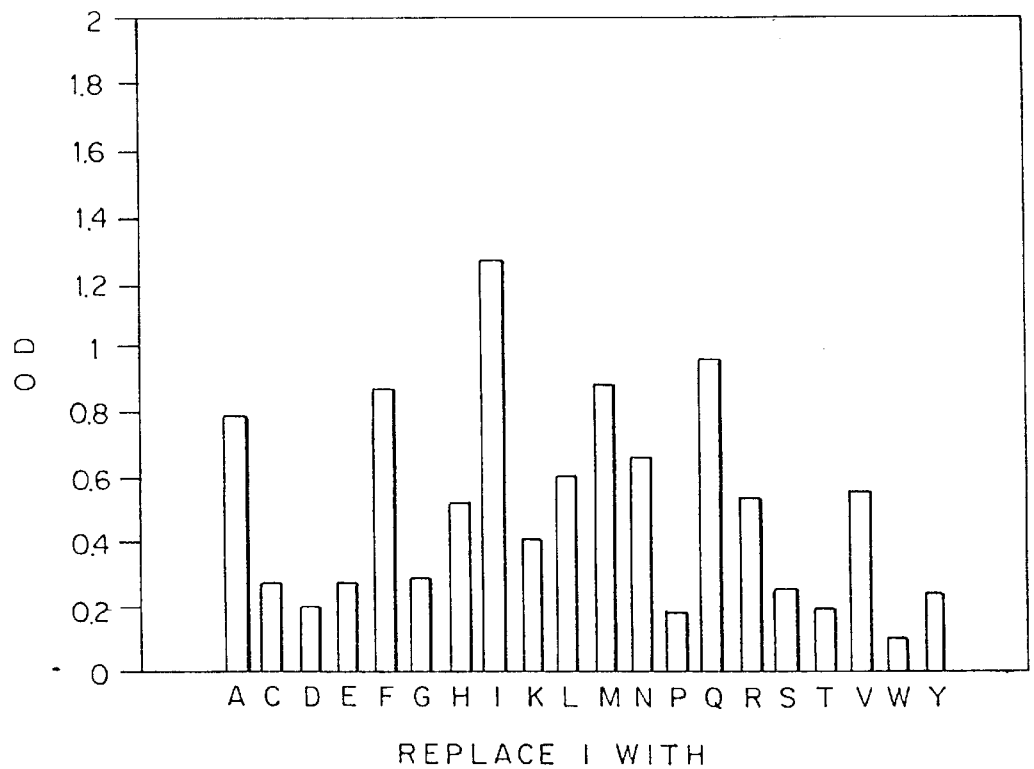
Figure 9C:
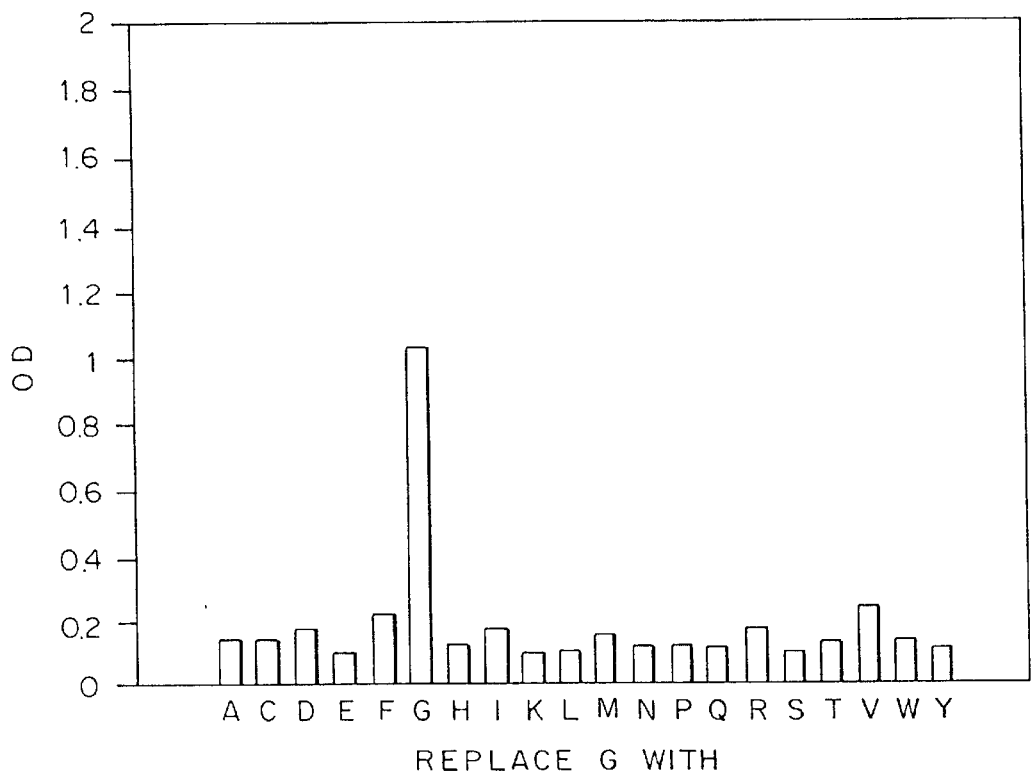
Figure 9D:
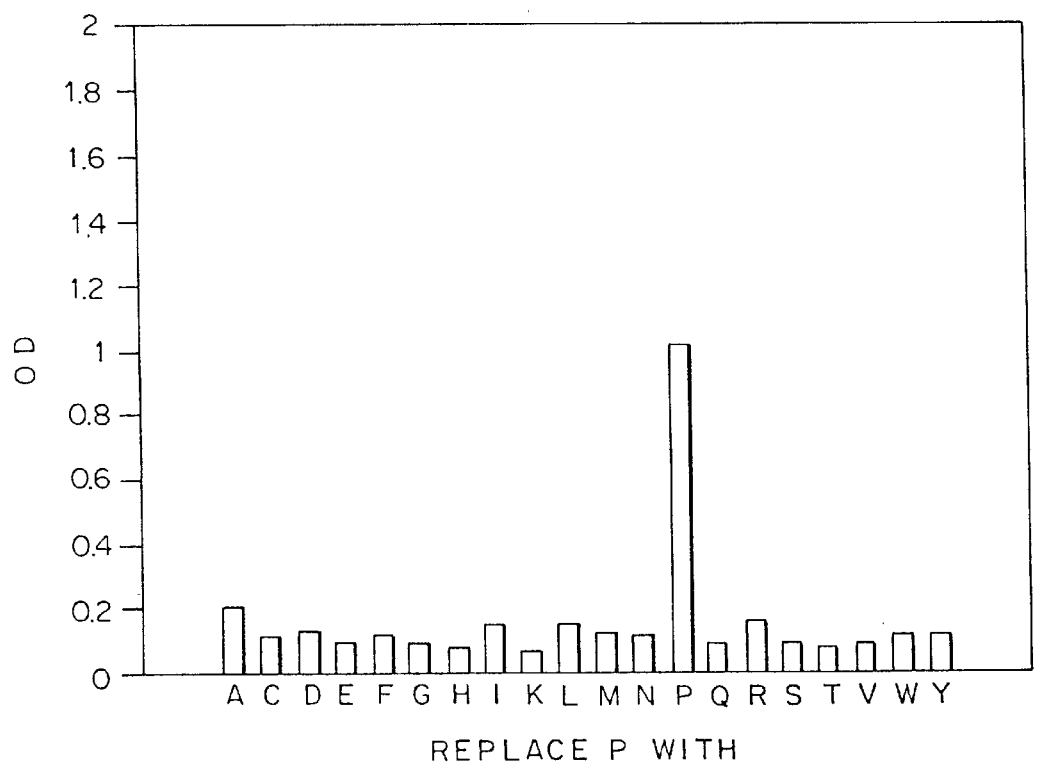
Figure 9E:
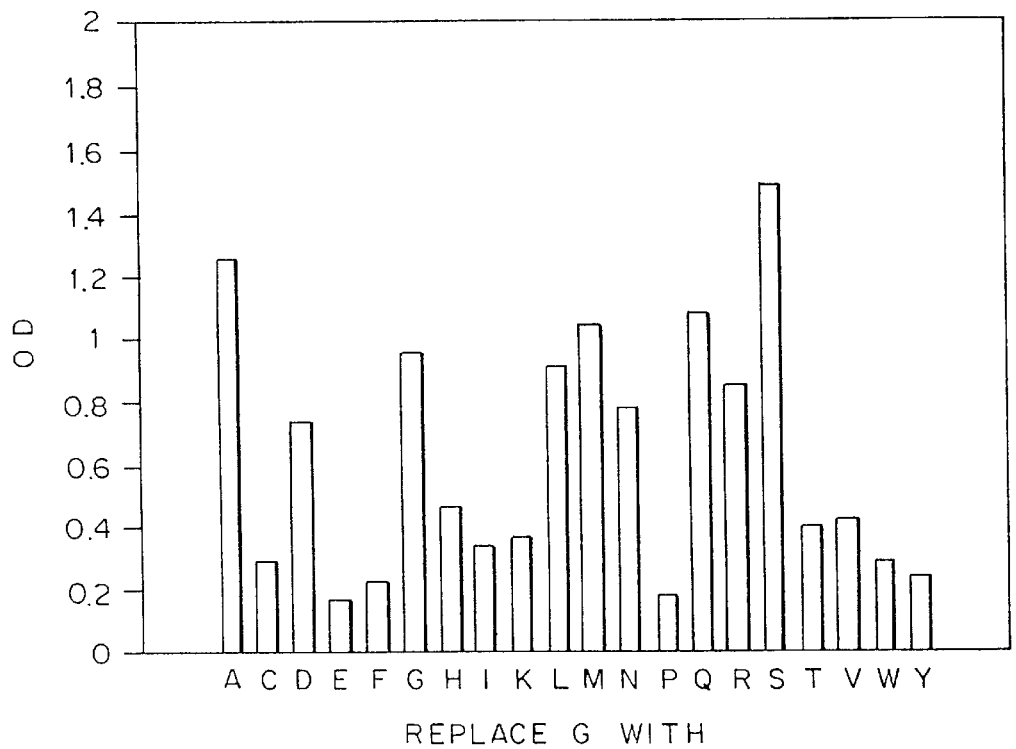
Figure 9F:
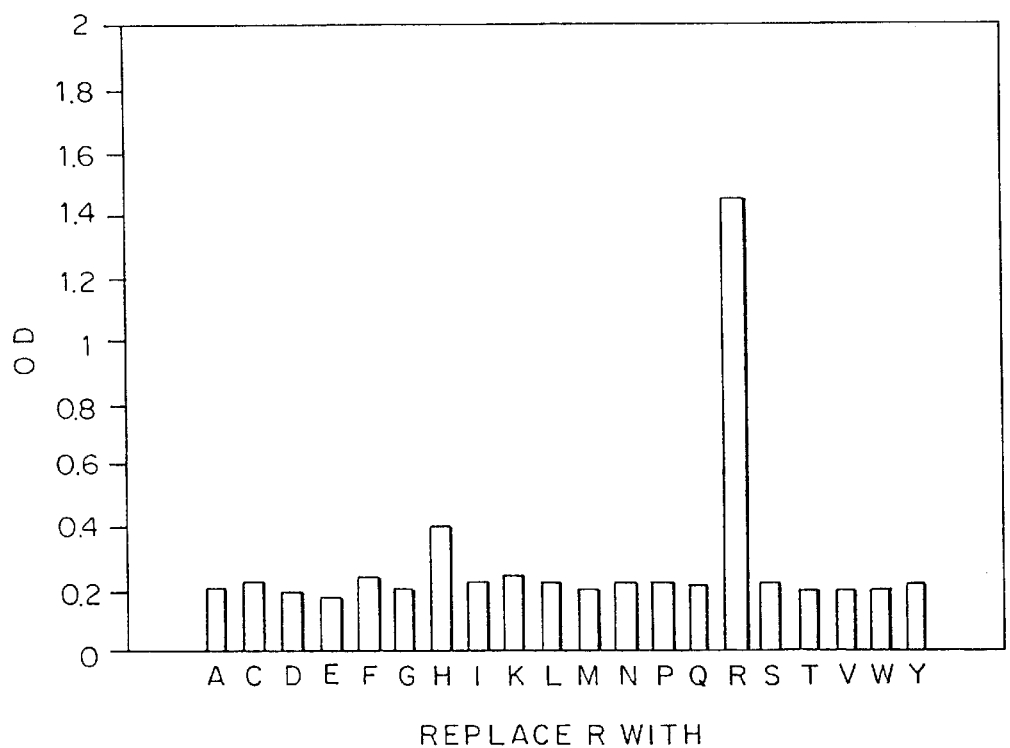

To determine which residues within the region were critical for binding to antibody 447-D, a series of hexapeptides were synthesized on pins, as above, such that each position in the HIGPGR (residues 13–18 of SEQ ID NO:1) hexapeptide was substituted individually with each of 19 amino acids. Thus, 115 hexapeptides were synthesized and tested with 447-D at a concentration of 10 µg/ml. The results, shown in FIGS. 9A and 9B, suggest that the H, the I and the second G (first, second and fifth positions) of HIGPGR (residues 13–18 of SEQ ID NO:1) can be varied considerably without loss of detectable reactivity with the antibody. It is interesting to note that the substitutions in this region which destroy reactivity with 447-D, e.g., substitution of C, D or E for I at the second position, are rarely or never found in HIV isolates sequenced to date (Myers, G. et al., Human Retroviruses and AIDS, Theoretical Biology and Biophysics, Los Alamos, 1990; LaRosa, J. G. et al., *Science* 249:932 (1990)). Importantly, the third, fourth and sixth positions of this hexapeptide could not be changed without abrogating antibody binding. These results indicate that the core epitope recognized by 447-D is most correctly represented as GPXR (SEQ ID NO:11) (where X denotes any amino acid).

It has been thought for some time that peptides comprising 3–7 amino acids fit within and bind to an antibody combining site (Schlossman, S. F. and Levine, H., *J. Immunol.*, 98: 211–9 (1967)). While the antigen combining site of 447-D appeared to bind to a tetrapeptide, experiments were performed to test whether amino acid residues at positions outside the GPGR motif, or whether general protein conformation, contributed to the binding of this antibody to its epitope.

The affinity of 447-D for various ligands in solution at equilibrium was determined using the method of Friguet et al. (supra). The dissociation constant, $K_d$ was calculated for the binding of 447-D to: (a) synthetic 20- and 22-mer V3 peptides of isolates MN, SF-2 and HXB2; (b) recombinant gp120$_{SF-2}$ (produced in CHO cells and obtained from Dr. Nancy Haigwood, Chiron Corporation, Albany, Calif.); and (c) recombinant gp120$_{IIIB}$ (produced from baculovirus vectors and purchased from Repligen Corporation, Cambridge, Mass.).

The results are summarized in Table 13, below. Although the V3 peptide of MN, SF-2 and HXB2 all contain GPGR (residues 15–18 of SEQ ID NO:1), there is a 43-fold difference in the $K_d$ of 447-D for these peptides. Moreover, the binding of the antibody to rgp120$_{SF-2}$ is 90-fold stronger than for V3$_{SF-2}$. The binding of the antibody to rgp120$_{IIIB}$ is six-fold stronger than binding to the V3$_{IIIB}$ peptide.

TABLE 13

Immunochemical and Biological Characteristics of Human mAb 447-D

| Virus | $K_d{}^a$ ($\times 10^{-6}$M) | | Neutralization Dose ($\mu$g/ml) | |
| --- | --- | --- | --- | --- |
| Isolate | V3 | rgp120 | 50% | 90% |
| MN | 0.56 | NA$^b$ | 0.052 | 0.9 |
| SF-2 | 0.9 | 0.01 | ND | ND |
| HXB2 | 24.0 | 3.9 | 1.8 | * |

$^a$The $K_d$ was determined as described above using 20- and 21-mers of the relevant V3 peptide and rgp120 from MN, SF-2 or HXB2. Neutralization was according to Nara et al. (supra).
$^b$Recombinant gp120$_{MN}$ was not available
*447-D produced 71% neutralization of IIIB in cultures when used at a maximum concentration of 10 $\mu$g/ml

EXAMPLE VII

Broadly Reactive Anti-V3 Antibodies in Human Sera

Tests were performed to see whether sera of HIV-infected subjects contained antibodies having reactivity similar to 447-D. Sera from 29 patients at various stages of HIV infection were tested for inhibition of binding of biotinlabelled 447-D to the V3$_{MN}$ 23-mer peptide in an ELISA. The 50% inhibition titers ranged from <1:2 to 1:256. These are remarkably low when compared to mean titers of 1:220,000 and 1:2,220 obtained by similar methods for binding to two epitopes of gp41 (Geysen et al., supra). However, as shown in Table 14, there was no correlation between disease progression (measured as the number of CD4+ cells) and the titer of antibodies blocking the binding of 447-D. This lack of correlation may not be surprising given that protection against HIV infection has been associated with certain minimum levels of antibodies in two passive immunization studies (Prince, A. M. et al., *Vaccines 90: Modern Approaches to New Vaccines Including Prevention of AIDS*, Brown, F. (ed.), Cold Spring Harbor Laboratory Press, Cold Spring Harbor, N.Y., 1990; Emini, E. A. et al., *J. Virol.* 64:3674 (1990)). Therefore, if neutralizing antibody levels are below a protective threshold, no correlation with disease progression would be expected.

TABLE 14

Titration of Serum Antibodies which Inhibit the Binding of 447-D to the V3$_{MN}$ Peptide

| HIV Status | Number of Subjects | CD4 cell count (cell/mm$^3$) | 50% Inhibitory Titer Geometric Mean (Range) |
| --- | --- | --- | --- |
| Positive | 12 | 0–250 | 1:24 (<1:2–1:256) |
| | 4 | 251–500 | 1:16 (1:8–1:32) |
| | 8 | 501–750 | 1:45 (1:8–1:128) |
| | 5 | >751 | 1:49 (1:16–1:128) |
| Negative | Serum pool | ND | undetectable |

ELISA plates were coated with V3$_{MN}$ peptide and incubated with diluted human serum. Thereafter, biotin-labelled 447-D was added and the reaction was developed with avidin, biotinylated horseradish peroxidase and a chromogenic substrate (2,2'azino-bis [3-ethylbenzthiazaline sulfonate) and peroxidase solution. The percent inhibition of binding was calculated as follows: $(A_{max} - A_x/A_{max} - A_{min}) \times 100$ where $A_{max}$ is absorbance inthe presence of 15 $\mu$g/ml 447-D (which results in maximal inhibition and minimum binding).

These results suggest that HIV-1 infected individuals have antibodies which are broadly cross-reactive and which have the characteristics and specificity of potent neutralizing antibodies specific for the V3 region of gp120. However, antibodies having these characteristics are present at extremely low levels in infected individuals, apparently below the necessary protective threshold.

Thus, the novel human mAbs and cell lines of the present invention, in particular 447-D, 694-D and other crossreactive antibodies, provide a therapeutic tool which may be used alone or in combination with other anti-HIV human mAbs in passive immunotherapy. Indeed, 447-D acts in synergy with human mAbs to the CD4-binding domain of gp120, such that significantly lower amounts of human mAb are needed for efficient virus neutralization (Buchbinder, A. et al., *AIDS Res. Hum. Retrovirol.* (1992); Zolla-Pazner et al., co-pending U.S. patent application Ser. No. 07/776,772, filed Oct. 15, 1991, which is hereby incorporated by reference).

Taken together, these results indicate that 447-D and 694-D are protective antibodies capable of neutralizing a number of divergent HIV-1 strains. These antibodies, like antibodies to many viral pathogens, have utility as immunotherapeutic products for various susceptible individuals such as health care workers coming in contact with HIV, in the prevention of maternal transmission of HIV to the fetus, and in halting the spread of virus in an already infected individual.

EXAMPLE VIII

Sequence Analysis of 447-D and 694-D

The DNA of the heterohybridoma cells which produce 447-D and 694-D were analyzed and the portions coding for the light chain of the variable domain ($V_L$) and the heavy chain of the variable domain ($V_H$) were sequenced and the corresponding amino acid sequence of the polypeptides coded thereby were determined. These sequences are shown in FIGS. 10–13.

The references cited above are all incorporated by reference herein, whether specifically incorporated or not.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the inventions following, in general, the principles of the invention and including such departures from the present disclosure as come within known or customary practice within the art to which the invention pertains and as may be applied to the essential features hereinbefore set forth as follows in the scope of the appended claims.

DEPOSITS

The following illustrative cell lines secreting human monoclonal antibodies specific for HIV-1 gp120 neutralizing epitopes were deposited at the ATCC, Rockville, Maryland, prior to the filing date of priority application, Ser. No. 07/538,451, under the requirements for a U.S. Patent Deposit.

1. 257-2: EBV transformed human lymphocyte line producing a human $IgG_1$, lambda antibody (ATCC accession #CRL 10483)
2. 268-11: EBV transformed human lymphocyte line producing a human $IgG_1$, lambda antibody (ATCC accession #CRL 10482)
3. 257-2D (also designated 257-D): Human×Human× Mouse Heterohybridoma cell line producing a human $IgG_1$, lambda antibody (ATCC accession #HB 10480)
4. 268-11D (also designated 268-D): Human×Human× Mouse Heterohybridoma cell line producing a human $IgG_1$, lambda antibody (ATCC accession #HB 10481)

The following illustrative cell line was deposited on Apr. 9, 1991, prior to the filing date of parent application Ser. No. 07/684,090, at the American Type Culture Collection, 12301 Parklawn Dr., Rockville, Md. 20852, under the requirements for a U.S. Patent Deposit:

5. 447-D (also referred to as 447-D): Human×Human× Mouse Heterohybridoma cell line producing a human $IgG_3$, lambda antibody (ATCC accession #HB 10725)

A progeny of this same hybridoma, hybridoma 447-52D IV, was later deposited at the American Type Culture Collection on Oct. 3, 1991, meeting all of the requirements for a deposit under the Budapest Treaty under ATCC accession #10891.

The following illustrative cell line was deposited on Apr. 22, 1992, at the American Type Culture Collection, 12301 Parklawn Drive, Rockville, Md. 20852, meeting all of the requirements for a deposit under the Budapest Treaty:

6. 694/98-D (also referred to as 694-D) Human×Human× Mouse heterohybridoma cell line producing a human IgG1 antibody (ATCC accession no. HB 11024.

SEQUENCE LISTING (1) GENERAL INFORMATION:

(iii) NUMBER OF SEQUENCES: 22

(2) INFORMATION FOR SEQ ID NO:1:

(i) SEQUENCE CHARACTERISTICS:
      (A) LENGTH: 35 amino acids
      (B) TYPE: amino acid
      (C) STRANDEDNESS: single
      (D) TOPOLOGY: linear (ii) MOLECULE TYPE: peptide (v) FRAGMENT TYPE: internal (vi) ORIGINAL SOURCE:
      (A) ORGANISM: Homo sapiens
      (C) INDIVIDUAL ISOLATE: MN (ix) FEATURE:
      (A) NAME/KEY: Peptide
      (B) LOCATION: 1..35
      (D) OTHER INFORMATION: /label= gp120MN-V3-LOOP
          /note= "This sequence corresponds to amino acids
          301 to 335 of gp120 from the MN isolate."

(xi) SEQUENCE DESCRIPTION: SEQ ID NO:1:

```
Cys Thr Arg Pro Asn Tyr Asn Lys Arg Lys Arg Ile His Ile Gly Pro
1               5                   10                  15

Gly Arg Ala Phe Tyr Thr Thr Lys Asn Ile Ile Gly Thr Ile Arg Gln
            20                  25                  30

Ala His Cys
        35
```

(2) INFORMATION FOR SEQ ID NO:2:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Homo sapiens
        (C) INDIVIDUAL ISOLATE: IIIB (ix) FEATURE:
        (A) NAME/KEY: Peptide
        (B) LOCATION: 1..22
        (D) OTHER INFORMATION: /note= "This sequence corresponds
            to 303 to 324 of gp120 from the IIIB isolate."

(xi) SEQUENCE DESCRIPTION: SEQ ID NO:2:

```
Thr Arg Lys Ser Ile Arg Ile Gln Arg Gly Pro Gly Arg Ala Phe Val
1               5                   10                  15

Thr Ile Gly Lys Ile Gly
            20
```

(2) INFORMATION FOR SEQ ID NO:3:

(i) SEQUENCE CHARACTERISTICS:
        (A) LENGTH: 396 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..396

(xi) SEQUENCE DESCRIPTION: SEQ ID NO:3:

```
ATG GCC GGC TCC CCT CTC CTC CTC ACC CTT CTC ATT CAC TGC ACA GGG     48
Met Ala Gly Ser Pro Leu Leu Leu Thr Leu Leu Ile His Cys Thr Gly
1               5                   10                  15

TCC TGG GCC CAG TCT GTG TTG ACG CAG CCG CCC TCA GTG TCT GCG GCC     96
Ser Trp Ala Gln Ser Val Leu Thr Gln Pro Pro Ser Val Ser Ala Ala
                20                  25                  30

CCA GGA CAG AAG GTC ACC ATC TCC TGC TCT GGA AGC AGC TCC AAC ATT    144
Pro Gly Gln Lys Val Thr Ile Ser Cys Ser Gly Ser Ser Ser Asn Ile
            35                  40                  45

CCC AAT AAT TAT GTA TTG TGG TAC CAG CAG TTC CCA GGA ACA GCC CCC    192
Pro Asn Asn Tyr Val Leu Trp Tyr Gln Gln Phe Pro Gly Thr Ala Pro
        50                  55                  60

AAA CTC CTC ATT TAT GGC AAT AAT AAG CGA CCC TCA GGG ATT CCT GAC    240
Lys Leu Leu Ile Tyr Gly Asn Asn Lys Arg Pro Ser Gly Ile Pro Asp
65                  70                  75                  80

CGA TTC TCT GGC TCC AAG TCT GGC ACG TCA GCC ACC CTG GGC ATC ACC    288
Arg Phe Ser Gly Ser Lys Ser Gly Thr Ser Ala Thr Leu Gly Ile Thr
                85                  90                  95

GGA CTC CAG ACT GGG GAC GAG GCC GAT TAT TTC TGC GCA ACA TGG GAT    336
Gly Leu Gln Thr Gly Asp Glu Ala Asp Tyr Phe Cys Ala Thr Trp Asp
            100                 105                 110

AGC GGC CTG AGT GCT GAT TGG GTG TTC GGC GGA GGG ACC AAG CTG ACC    384
Ser Gly Leu Ser Ala Asp Trp Val Phe Gly Gly Gly Thr Lys Leu Thr
        115                 120                 125
```

```
GTC CTA AGT CAT                                                        396
Val Leu Ser His
    130
```

(2) INFORMATION FOR SEQ ID NO:4:

(i) SEQUENCE CHARACTERISTICS:
        (A) LENGTH: 132 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Gly Ser Pro Leu Leu Thr Leu Leu Ile His Cys Thr Gly
  1               5                  10                  15

Ser Trp Ala Gln Ser Val Leu Thr Gln Pro Pro Ser Val Ser Ala Ala
                 20                  25                  30

Pro Gly Gln Lys Val Thr Ile Ser Cys Ser Gly Ser Ser Ser Asn Ile
             35                  40                  45

Pro Asn Asn Tyr Val Leu Trp Tyr Gln Gln Phe Pro Gly Thr Ala Pro
 50                  55                  60

Lys Leu Leu Ile Tyr Gly Asn Asn Lys Arg Pro Ser Gly Ile Pro Asp
 65                  70                  75                  80

Arg Phe Ser Gly Ser Lys Ser Gly Thr Ser Ala Thr Leu Gly Ile Thr
                 85                  90                  95

Gly Leu Gln Thr Gly Asp Glu Ala Asp Tyr Phe Cys Ala Thr Trp Asp
            100                 105                 110

Ser Gly Leu Ser Ala Asp Trp Val Phe Gly Gly Gly Thr Lys Leu Thr
            115                 120                 125

Val Leu Ser His
    130
```

(2) INFORMATION FOR SEQ ID NO:5:

(i) SEQUENCE CHARACTERISTICS:
        (A) LENGTH: 450 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..450

(xi) SEQUENCE DESCRIPTION: SEQ ID NO:5:

```
ATG GTG TTT GGG CTG AGC TGG ATT TTC CTC GCT GCT ATT TTA AAA GGT      48
Met Val Phe Gly Leu Ser Trp Ile Phe Leu Ala Ala Ile Leu Lys Gly
  1               5                  10                  15

GTC CAG TGT GAG GTG CAG CTG GTG GAG TCT GGG GGA GCC TTG GTA AAG      96
Val Gln Cys Glu Val Gln Leu Val Glu Ser Gly Gly Ala Leu Val Lys
                 20                  25                  30

CCT GGG GGG TCC CTC AGA CTC ACC TGT GTA GCC TCT GGT TTC ACG TTC     144
Pro Gly Gly Ser Leu Arg Leu Thr Cys Val Ala Ser Gly Phe Thr Phe
             35                  40                  45

AGT GAT GTC TGG CTG AAC TGG GTC CTC CAG GCT CCA GGG AAG GGG CTG     192
Ser Asp Val Trp Leu Asn Trp Val Leu Gln Ala Pro Gly Lys Gly Leu
 50                  55                  60

GAG CGG GTC GGC CGT ATT AAA AGC AGA ACT GAT GGT GGG ACA ACA GAC     240
Glu Arg Val Gly Arg Ile Lys Ser Arg Thr Asp Gly Gly Thr Thr Asp
 65                  70                  75                  80
```

```
TAC GCT GCA TCC GTG AAA GGC AGA TTC ACC ATC TCA AGA GAT GAC TCA        288
Tyr Ala Ala Ser Val Lys Gly Arg Phe Thr Ile Ser Arg Asp Asp Ser
                85                  90                  95

AAA AAC ACG CTA TAT CTG CAA ATG AAT AGC CTG AAA ACC GAG GAC ACA        336
Lys Asn Thr Leu Tyr Leu Gln Met Asn Ser Leu Lys Thr Glu Asp Thr
            100                 105                 110

GCC GTT TAT TCC TGC ACC ACA GAT GGT TTT ATT ATG ATT CGG GGA GTC        384
Ala Val Tyr Ser Cys Thr Thr Asp Gly Phe Ile Met Ile Arg Gly Val
        115                 120                 125

TCC GAG GAC TAC TAC TAC TAC ATG GAC GTT TGG CCC AAA GGG ACC            432
Ser Glu Asp Tyr Tyr Tyr Tyr Met Asp Val Trp Pro Lys Gly Thr
130                 135                 140

ACG GTC ACC GTG AGC TCA                                                450
Thr Val Thr Val Ser Ser
145                 150
```

(2) INFORMATION FOR SEQ ID NO:6:

(i) SEQUENCE CHARACTERISTICS:
        (A) LENGTH: 150 amino acids
        (B) TYPE: amino acid
        (D) TOPOLOGY: linear (ii) MOLECULE TYPE: protein (xi) SEQUENCE DESCRIPTION: SEQ ID NO:6:

```
Met Val Phe Gly Leu Ser Trp Ile Phe Leu Ala Ala Ile Leu Lys Gly
 1               5                  10                  15

Val Gln Cys Glu Val Gln Leu Val Glu Ser Gly Gly Ala Leu Val Lys
            20                  25                  30

Pro Gly Gly Ser Leu Arg Leu Thr Cys Val Ala Ser Gly Phe Thr Phe
        35                  40                  45

Ser Asp Val Trp Leu Asn Trp Val Leu Gln Ala Pro Gly Lys Gly Leu
    50                  55                  60

Glu Arg Val Gly Arg Ile Lys Ser Arg Thr Asp Gly Gly Thr Thr Asp
65                  70                  75                  80

Tyr Ala Ala Ser Val Lys Gly Arg Phe Thr Ile Ser Arg Asp Asp Ser
                85                  90                  95

Lys Asn Thr Leu Tyr Leu Gln Met Asn Ser Leu Lys Thr Glu Asp Thr
            100                 105                 110

Ala Val Tyr Ser Cys Thr Thr Asp Gly Phe Ile Met Ile Arg Gly Val
        115                 120                 125

Ser Glu Asp Tyr Tyr Tyr Tyr Met Asp Val Trp Pro Lys Gly Thr
130                 135                 140

Thr Val Thr Val Ser Ser
145                 150
```

(2) INFORMATION FOR SEQ ID NO:7:

(i) SEQUENCE CHARACTERISTICS:
        (A) LENGTH: 431 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..429

(xi) SEQUENCE DESCRIPTION: SEQ ID NO:7:

| | | | | | | | | | | | | | | | | |
|---|---|---|---|---|---|---|---|---|---|---|---|---|---|---|---|---|
| ATG | GCC | GGC | TCC | CCT | CTC | CTC | CTC | ACC | CTC | CTC | ACT | CTC | TGC | ACA | GGC | 48 |
| Met | Ala | Gly | Ser | Pro | Leu | Leu | Leu | Thr | Leu | Leu | Thr | Leu | Cys | Thr | Gly | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| TCT | GAG | GCC | TCC | TAT | GAG | CTG | ACA | CAG | CCA | CCC | TCG | GTG | TCA | GTG | TCC | 96 |
| Ser | Glu | Ala | Ser | Tyr | Glu | Leu | Thr | Gln | Pro | Pro | Ser | Val | Ser | Val | Ser | |
| | | | | | 20 | | | | | 25 | | | | | 30 | |

| | | | | | | | | | | | | | | | | |
|---|---|---|---|---|---|---|---|---|---|---|---|---|---|---|---|---|
| CCT | GGA | CAG | ACG | GCC | AGG | ATC | ACC | TGT | TCT | GGA | GAT | GCA | TTG | CCA | AAC | 144 |
| Pro | Gly | Gln | Thr | Ala | Arg | Ile | Thr | Cys | Ser | Gly | Asp | Ala | Leu | Pro | Asn | |
| | | | 35 | | | | | 40 | | | | | 45 | | | |

| | | | | | | | | | | | | | | | | |
|---|---|---|---|---|---|---|---|---|---|---|---|---|---|---|---|---|
| CAA | TAT | GTT | TAT | TGG | TAC | CAA | CAG | AGA | CCA | GGC | CAG | GCC | CCT | GTG | GTG | 192 |
| Gln | Tyr | Val | Tyr | Trp | Tyr | Gln | Gln | Arg | Pro | Gly | Gln | Ala | Pro | Val | Val | |
| | 50 | | | | | 55 | | | | | 60 | | | | | |

| | | | | | | | | | | | | | | | | |
|---|---|---|---|---|---|---|---|---|---|---|---|---|---|---|---|---|
| GTC | CTA | TAT | AAA | GAC | ACT | GAG | AGG | CCC | TCA | GGG | ATC | CCT | GAG | CGA | TTC | 240 |
| Val | Leu | Tyr | Lys | Asp | Thr | Glu | Arg | Pro | Ser | Gly | Ile | Pro | Glu | Arg | Phe | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| TCT | GGC | TCC | AGC | TCA | GGG | ACA | ACA | GTC | ACG | TTG | ACC | ATC | AGT | GGA | GTC | 288 |
| Ser | Gly | Ser | Ser | Ser | Gly | Thr | Thr | Val | Thr | Leu | Thr | Ile | Ser | Gly | Val | |
| | | | | 85 | | | | | 90 | | | | | 95 | | |

| | | | | | | | | | | | | | | | | |
|---|---|---|---|---|---|---|---|---|---|---|---|---|---|---|---|---|
| CAG | GCA | GAA | GAC | GAG | GCT | GAC | TAT | TAT | TGT | CAA | TCA | GCA | GAC | AAC | AGT | 336 |
| Gln | Ala | Glu | Asp | Glu | Ala | Asp | Tyr | Tyr | Cys | Gln | Ser | Ala | Asp | Asn | Ser | |
| | | | 100 | | | | | 105 | | | | | 110 | | | |

| | | | | | | | | | | | | | | | | |
|---|---|---|---|---|---|---|---|---|---|---|---|---|---|---|---|---|
| GGT | GCT | TAC | CCT | TTG | TTC | TTC | GGC | GGT | GGG | ACC | AAG | CTG | ACC | GTC | CTA | 384 |
| Gly | Ala | Tyr | Pro | Leu | Phe | Phe | Gly | Gly | Gly | Thr | Lys | Leu | Thr | Val | Leu | |
| | | | 115 | | | | | 120 | | | | | 125 | | | |

| | | | | | | | | | | | | | | |
|---|---|---|---|---|---|---|---|---|---|---|---|---|---|---|
| CGT | CAG | CCC | AAG | GCT | GCC | CCC | TCG | GTC | ACT | CTG | TTC | CCG | CCC | TCC | 429 |
| Arg | Gln | Pro | Lys | Ala | Ala | Pro | Ser | Val | Thr | Leu | Phe | Pro | Pro | Ser | |
| 130 | | | | | 135 | | | | | 140 | | | | | |

TC                                                                                                           431

(2) INFORMATION FOR SEQ ID NO:8:

(i) SEQUENCE CHARACTERISTICS:
        (A) LENGTH: 143 amino acids
        (B) TYPE: amino acid
        (D) TOPOLOGY: linear (ii) MOLECULE TYPE: protein (xi) SEQUENCE DESCRIPTION: SEQ ID NO:8:

| | | | | | | | | | | | | | | | |
|---|---|---|---|---|---|---|---|---|---|---|---|---|---|---|---|
| Met | Ala | Gly | Ser | Pro | Leu | Leu | Leu | Thr | Leu | Leu | Thr | Leu | Cys | Thr | Gly |
| 1 | | | | 5 | | | | | 10 | | | | | 15 | |

| | | | | | | | | | | | | | | | |
|---|---|---|---|---|---|---|---|---|---|---|---|---|---|---|---|
| Ser | Glu | Ala | Ser | Tyr | Glu | Leu | Thr | Gln | Pro | Pro | Ser | Val | Ser | Val | Ser |
| | | | | | 20 | | | | | 25 | | | | | 30 |

| | | | | | | | | | | | | | | | |
|---|---|---|---|---|---|---|---|---|---|---|---|---|---|---|---|
| Pro | Gly | Gln | Thr | Ala | Arg | Ile | Thr | Cys | Ser | Gly | Asp | Ala | Leu | Pro | Asn |
| | | | 35 | | | | | 40 | | | | | 45 | | |

| | | | | | | | | | | | | | | | |
|---|---|---|---|---|---|---|---|---|---|---|---|---|---|---|---|
| Gln | Tyr | Val | Tyr | Trp | Tyr | Gln | Gln | Arg | Pro | Gly | Gln | Ala | Pro | Val | Val |
| | 50 | | | | | 55 | | | | | 60 | | | | |

| | | | | | | | | | | | | | | | |
|---|---|---|---|---|---|---|---|---|---|---|---|---|---|---|---|
| Val | Leu | Tyr | Lys | Asp | Thr | Glu | Arg | Pro | Ser | Gly | Ile | Pro | Glu | Arg | Phe |
| 65 | | | | | 70 | | | | | 75 | | | | | 80 |

| | | | | | | | | | | | | | | | |
|---|---|---|---|---|---|---|---|---|---|---|---|---|---|---|---|
| Ser | Gly | Ser | Ser | Ser | Gly | Thr | Thr | Val | Thr | Leu | Thr | Ile | Ser | Gly | Val |
| | | | | 85 | | | | | 90 | | | | | 95 | |

| | | | | | | | | | | | | | | | |
|---|---|---|---|---|---|---|---|---|---|---|---|---|---|---|---|
| Gln | Ala | Glu | Asp | Glu | Ala | Asp | Tyr | Tyr | Cys | Gln | Ser | Ala | Asp | Asn | Ser |
| | | | 100 | | | | | 105 | | | | | 110 | | |

| | | | | | | | | | | | | | | | |
|---|---|---|---|---|---|---|---|---|---|---|---|---|---|---|---|
| Gly | Ala | Tyr | Pro | Leu | Phe | Phe | Gly | Gly | Gly | Thr | Lys | Leu | Thr | Val | Leu |
| | | | 115 | | | | | 120 | | | | | 125 | | |

| | | | | | | | | | | | | | | |
|---|---|---|---|---|---|---|---|---|---|---|---|---|---|---|
| Arg | Gln | Pro | Lys | Ala | Ala | Pro | Ser | Val | Thr | Leu | Phe | Pro | Pro | Ser |
| 130 | | | | | 135 | | | | | 140 | | | | | |

(2) INFORMATION FOR SEQ ID NO:9:

(i) SEQUENCE CHARACTERISTICS:
        (A) LENGTH: 423 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..423

(xi) SEQUENCE DESCRIPTION: SEQ ID NO:9:

```
ATG GAC ATA CTT TGT ACC ACG CTC CTG CTG CTG ACC ATC CCT TCA TGG      48
Met Asp Ile Leu Cys Thr Thr Leu Leu Leu Leu Thr Ile Pro Ser Trp
1               5                  10                  15

GTC TTG TCC CAG ATC ACC TTG AAG GAG TCT GGT CCT ACG CTA GTG AAA      96
Val Leu Ser Gln Ile Thr Leu Lys Glu Ser Gly Pro Thr Leu Val Lys
            20                  25                  30

CCC ACA CAG ACC CTC ACA CTG ACC TGC ACC TTC TCT GGG TTC TCG CTC     144
Pro Thr Gln Thr Leu Thr Leu Thr Cys Thr Phe Ser Gly Phe Ser Leu
        35                  40                  45

AGT ACT AGT GGA GTG GGT GTG GCC TGG ATC CGT CAG CCC CCA GGA AAG     192
Ser Thr Ser Gly Val Gly Val Ala Trp Ile Arg Gln Pro Pro Gly Lys
    50                  55                  60

GCC CTG GAG TGG CTT GCA CTC ATT TAT TGG GAT GAT GAT AAG CGC TAC     240
Ala Leu Glu Trp Leu Ala Leu Ile Tyr Trp Asp Asp Asp Lys Arg Tyr
65                  70                  75                  80

AAC CCA ACT CTG AAC AGC AGG CTC ACC ATC GCC CAG GAC ACC GCC AAG     288
Asn Pro Thr Leu Asn Ser Arg Leu Thr Ile Ala Gln Asp Thr Ala Lys
                85                  90                  95

AAC CAG GTG GTC CTT ACA ATG ACC AAC ATG GAC CCT GTG GAC ACA GGC     336
Asn Gln Val Val Leu Thr Met Thr Asn Met Asp Pro Val Asp Thr Gly
            100                 105                 110

ACA TAT TAC TGT GCA CAC TTA GGT GGA TAT GAT GGC TAC GAT TTC GCT     384
Thr Tyr Tyr Cys Ala His Leu Gly Gly Tyr Asp Gly Tyr Asp Phe Ala
        115                 120                 125

GAC AAC TGG GGC CAG GGA ATC CTG GTC ACC GTC GCC TCN                 423
Asp Asn Trp Gly Gln Gly Ile Leu Val Thr Val Ala Ser
    130                 135                 140
```

(2) INFORMATION FOR SEQ ID NO:10:

(i) SEQUENCE CHARACTERISTICS:
        (A) LENGTH: 141 amino acids
        (B) TYPE: amino acid
        (D) TOPOLOGY: linear (ii) MOLECULE TYPE: protein (xi) SEQUENCE DESCRIPTION: SEQ ID NO:10:

```
Met Asp Ile Leu Cys Thr Thr Leu Leu Leu Leu Thr Ile Pro Ser Trp
1               5                  10                  15

Val Leu Ser Gln Ile Thr Leu Lys Glu Ser Gly Pro Thr Leu Val Lys
            20                  25                  30

Pro Thr Gln Thr Leu Thr Leu Thr Cys Thr Phe Ser Gly Phe Ser Leu
        35                  40                  45

Ser Thr Ser Gly Val Gly Val Ala Trp Ile Arg Gln Pro Pro Gly Lys
    50                  55                  60

Ala Leu Glu Trp Leu Ala Leu Ile Tyr Trp Asp Asp Asp Lys Arg Tyr
65                  70                  75                  80
```

```
Asn Pro Thr Leu Asn Ser Arg Leu Thr Ile Ala Gln Asp Thr Ala Lys
            85                  90                  95

Asn Gln Val Val Leu Thr Met Thr Asn Met Asp Pro Val Asp Thr Gly
            100                 105                 110

Thr Tyr Tyr Cys Ala His Leu Gly Gly Tyr Asp Gly Tyr Asp Phe Ala
            115                 120                 125

Asp Asn Trp Gly Gln Gly Ile Leu Val Thr Val Ala Ser
    130                 135                 140
```

(2) INFORMATION FOR SEQ ID NO:11:

(i) SEQUENCE CHARACTERISTICS:
        (A) LENGTH: 4 amino acids
        (B) TYPE: amino acid
        (D) TOPOLOGY: linear (ii) MOLECULE TYPE: peptide (xi) SEQUENCE DESCRIPTION: SEQ ID NO:11:

```
Gly Pro Xaa Arg
1
```

(2) INFORMATION FOR SEQ ID NO:12:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Homo sapiens
        (C) INDIVIDUAL ISOLATE: RF (ix) FEATURE:
        (A) NAME/KEY: Peptide
        (B) LOCATION: 1..24
        (D) OTHER INFORMATION: /note= "This sequence corresponds
            to amino acids 301 to 324 of gp120 from the RF
            isolate."

(xi) SEQUENCE DESCRIPTION: SEQ ID NO:12:

```
Asn Asn Thr Arg Lys Ser Ile His Ile Thr Lys Gly Pro Gly Arg Val
1               5                   10                  15

Ile Tyr Ala Thr Gly Gln Ile Ile
            20
```

(2) INFORMATION FOR SEQ ID NO:13:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: homo sapien
        (C) INDIVIDUAL ISOLATE: NY5

(ix) FEATURE:
        (A) NAME/KEY: Peptide
        (B) LOCATION: 1..6
        (D) OTHER INFORMATION: /note= "This sequence is part of
            the V3 loop of gp120 from the NY5 isolate."

(xi) SEQUENCE DESCRIPTION: SEQ ID NO:13:

Gly Pro Gly Arg Thr Leu
1               5

(2) INFORMATION FOR SEQ ID NO:14:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Homo sapiens
        (C) INDIVIDUAL ISOLATE: CDC4C (ix) FEATURE:
        (A) NAME/KEY: Peptide
        (B) LOCATION: 1..6
        (D) OTHER INFORMATION: /note= "This sequence corresponds
            to the V3 loop of gp120 of the CDC4 isol..."

(xi) SEQUENCE DESCRIPTION: SEQ ID NO:14:

Gly Pro Gly Arg Val Trp
1               5

(2) INFORMATION FOR SEQ ID NO:15:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Homo sapiens
        (C) INDIVIDUAL ISOLATE: SF33

(ix) FEATURE:
        (A) NAME/KEY: Peptide
        (B) LOCATION: 1..6
        (D) OTHER INFORMATION: /note= "This sequence corresponds
            to the V3 loop of gp120 of the SF33 isol..."

(xi) SEQUENCE DESCRIPTION: SEQ ID NO:15:

Gly Pro Gly Lys Val Leu
1               5

(2) INFORMATION FOR SEQ ID NO:16:

(i) SEQUENCE CHARACTERISTICS:
        (A) LENGTH: 6 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Homo sapiens
        (C) INDIVIDUAL ISOLATE: ELI (ix) FEATURE:
        (A) NAME/KEY: Peptide
        (B) LOCATION: 1..6
        (D) OTHER INFORMATION: /note= "This sequence corresponds
            to the V3 loop of gp120 of the ELI isola..."

(xi) SEQUENCE DESCRIPTION: SEQ ID NO:16:

Gly Leu Gly Gln Ser Leu
1               5

(2) INFORMATION FOR SEQ ID NO:17:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (v) FRAGMENT TYPE: internal (vi) ORIGINAL SOURCE:
         (A) ORGANISM: Homo sapiens
         (C) INDIVIDUAL ISOLATE: SF-2

(ix) FEATURE:
         (A) NAME/KEY: Peptide
         (B) LOCATION: 1..22
         (D) OTHER INFORMATION: /note= "This sequence corresponds
             to amino acids 303 to 324 of the V3 loop of gp120
             from the SF-2 isolate."

(xi) SEQUENCE DESCRIPTION: SEQ ID NO:17:

Asn Asn Thr Arg Lys Ser Ile Tyr Ile Gly Pro Gly Arg Ala Phe His
1               5                  10                  15

Thr Thr Gly Arg Ile Ile
            20

(2) INFORMATION FOR SEQ ID NO:18:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (v) FRAGMENT TYPE: internal (vi) ORIGINAL SOURCE:
         (A) ORGANISM: Homo sapiens
         (C) INDIVIDUAL ISOLATE: AL-1

(ix) FEATURE:
         (A) NAME/KEY: Peptide
         (B) LOCATION: 1..22
         (D) OTHER INFORMATION: /note= "This sequence corresponds
             to the V3 loop of gp120 of the AL-1 isol..."

(xi) SEQUENCE DESCRIPTION: SEQ ID NO:18:

Ile Tyr Arg Lys Gly Arg Ile His Ile Gly Pro Gly Arg Ala Phe His
1               5                  10                  15

Thr Thr Arg Gln Ile Ile
            20

(2) INFORMATION FOR SEQ ID NO:19:

(i) SEQUENCE CHARACTERISTICS:
         (A) LENGTH: 22 amino acids
         (B) TYPE: amino acid
         (D) TOPOLOGY: linear (ii) MOLECULE TYPE: peptide (v) FRAGMENT TYPE: internal

```
        (vi) ORIGINAL SOURCE:
              (A) ORGANISM: Homo sapiens
              (C) INDIVIDUAL ISOLATE: DU 6587-5

(ix) FEATURE:
              (A) NAME/KEY: Peptide
              (B) LOCATION: 1..22
              (D) OTHER INFORMATION: /note= "This sequence corresponds
                    to the V3 loop of the gp120 from the DU 6587-5
                    isolate."

(xi) SEQUENCE DESCRIPTION: SEQ ID NO:19:

Ser Asn Val Arg Asn Arg Ile His Ile Gly Pro Gly Arg Ala Phe His
1               5                   10                  15

Thr Thr Lys Arg Ile Thr
            20

(2) INFORMATION FOR SEQ ID NO:20:

(i) SEQUENCE CHARACTERISTICS:
              (A) LENGTH: 22 amino acids
              (B) TYPE: amino acid
              (D) TOPOLOGY: linear (ii) MOLECULE TYPE: peptide (v) FRAGMENT TYPE: internal (vi) ORIGINAL SOURCE:
              (A) ORGANISM: Homo sapiens
              (C) INDIVIDUAL ISOLATE: WMJ-2

(ix) FEATURE:
              (A) NAME/KEY: Protein
              (B) LOCATION: 1..22
              (D) OTHER INFORMATION: /note= "This sequence corresponds
                    to V3 loop of gp120 from the WMJ-2 isola..."

(xi) SEQUENCE DESCRIPTION: SEQ ID NO:20:

Asn Asn Val Arg Arg Ser Leu Ser Ile Gly Pro Gly Arg Ala Phe Arg
1               5                   10                  15

Thr Arg Glu Ile Ile Gly
            20

(2) INFORMATION FOR SEQ ID NO:21:

(i) SEQUENCE CHARACTERISTICS:
              (A) LENGTH: 22 amino acids
              (B) TYPE: amino acid
              (D) TOPOLOGY: linear (ii) MOLECULE TYPE: peptide (v) FRAGMENT TYPE: internal (vi) ORIGINAL SOURCE:
              (A) ORGANISM: Homo sapiens
              (C) INDIVIDUAL ISOLATE: DU 7887-7

(ix) FEATURE:
              (A) NAME/KEY: Peptide
              (B) LOCATION: 1..22
              (D) OTHER INFORMATION: /note= "This sequence corresponds
                    to the V3 loop of gp120 from the DU 7887-7
                    isolate."

(xi) SEQUENCE DESCRIPTION: SEQ ID NO:21:

Asn Asn Thr Ser Arg Gly Ile Arg Ile Gly Pro Gly Arg Ala Ile Leu
1               5                   10                  15

Ala Thr Glu Arg Ile Ile
            20
```

-continued (2) INFORMATION FOR SEQ ID NO:22:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (v) FRAGMENT TYPE: internal (vi) ORIGINAL SOURCE:
        (A) ORGANISM: Homo sapiens
        (C) INDIVIDUAL ISOLATE: SF-162

(ix) FEATURE:
        (A) NAME/KEY: Peptide
        (B) LOCATION: 1..22
        (D) OTHER INFORMATION: /note= "This sequence corresponds
           to the V3 loop of gp120 from the SF-162 isolate."

(xi) SEQUENCE DESCRIPTION: SEQ ID NO:22:

```
Asn Asn Thr Arg Lys Ser Ile Thr Ile Gly Pro Gly Arg Ala Phe Tyr
1               5                   10                  15
Ala Thr Gly Asp Ile Ile
            20
```

What is claimed is:

1. A molecule capable of binding to a neutralizing epitope of the V3 loop of HIV-1 gp120, comprising:

(a) a human monoclonal antibody specific for a neutralizing epitope of the V3 loop of HIV-1 gp120 glycoprotein, which antibody is broadly reactive in that it immunologically binds and neutralizes at least two divergent HIV-1 isolates or strains, or (b) an antigen binding fragment of said human monoclonal antibody.

2. A molecule in accordance with claim 1, wherein said molecule comprises said human monoclonal antibody of (a).

3. A molecule in accordance with claim 1, wherein said human monoclonal antibody is the human monoclonal antibody designated 447-D produced by the cell line having ATCC Accession No. HB 10891.

4. A molecule in accordance with claim 1, wherein said human monoclonal antibody is the human monoclonal antibody designated 694-D produced by the cell line having ATCC Accession No. HB 11024.

5. A molecule in accordance with claim 1, selected from the group consisting of a molecule which comprises a polypeptide comprising the sequence of SEQ ID NO:4 associated with a polypeptide comprising the sequence of SEQ ID NO:6, and a molecule comprising a polypeptide comprising the sequence of SEQ ID NO:8 associated with a polypeptide comprising the sequence of SEQ ID NO:10.

6. A molecule in accordance with claim 1, wherein said molecule is a chimeric antibody, a single chain antibody or a chimeric T cell receptor.

7. A cell line which produces a molecule in accordance with claim 1.

8. A cell line which produces a human monoclonal antibody in accordance with claim 2.

9. A cell line in accordance with claim 8 which is a human-mouse heterohybridoma cell line.

10. A cell line in accordance with claim 8, which is the cell line designated 447-D having ATCC No. HB 10891.

11. A cell line in accordance with claim 8, which is the cell line designated 694-D having ATCC No. HB 11024.

12. A method of producing a human monoclonal antibody specific for a neutralizing epitope of the V3 loop of HIV-1 gp120 glycoprotein, which antibody is broadly reactive in that it immunologically binds and neutralizes at least two divergent HIV-1 isolates or strains, comprising:

causing the cell line in accordance with claim 8 to grow under conditions in which antibody is produced by said cells; and recovering said antibody from said cells.

13. A method for decreasing the likelihood of infection by HIV-1 of a subject at risk for HIV infection, or for treating a subject infected with HIV-1, comprising administering to said subject a therapeutically effective amount of a molecule according to claim 1.

14. A pharmaceutical composition comprising a molecule in accordance with claim 1 and a pharmaceutically acceptable excipient.

* * * * *